US009320419B2

(12) United States Patent
Kirma et al.

(10) Patent No.: US 9,320,419 B2
(45) Date of Patent: Apr. 26, 2016

(54) FLUID CHANNELING COMPONENT OF A MULTI-CAMERA ENDOSCOPE

(75) Inventors: Yaniv Kirma, Tzrufa (IL); Avi Levy, Herzliya (IL); Golan Salman, Atlit (IL); Amram Aizenfeld, Ramot Menashe (IL)

(73) Assignee: EndoChoice Innovation Center Ltd., Caesarea (IL)

( * ) Notice: Subject to any disclaimer, the term of this patent is extended or adjusted under 35 U.S.C. 154(b) by 173 days.

(21) Appl. No.: 13/992,021

(22) PCT Filed: Dec. 8, 2011

(86) PCT No.: PCT/IL2011/050050
§ 371 (c)(1),
(2), (4) Date: Jun. 6, 2013

(87) PCT Pub. No.: WO2012/077117
PCT Pub. Date: Jun. 14, 2012

(65) Prior Publication Data
US 2013/0274551 A1    Oct. 17, 2013

Related U.S. Application Data

(60) Provisional application No. 61/421,240, filed on Dec. 9, 2010.

(51) Int. Cl.
*A61B 1/04* (2006.01)
*A61B 1/12* (2006.01)
(Continued)

(52) U.S. Cl.
CPC ............. *A61B 1/126* (2013.01); *A61B 1/00073* (2013.01); *A61B 1/00091* (2013.01); *A61B 1/00094* (2013.01); *A61B 1/00096* (2013.01); *A61B 1/00177* (2013.01); *A61B 1/00181* (2013.01); *A61B 1/015* (2013.01);
(Continued)

(58) Field of Classification Search
USPC .......... 600/109, 113, 129–130, 156–157, 165, 600/170–171
See application file for complete search history.

(56) References Cited

U.S. PATENT DOCUMENTS

| 4,253,448 A | 3/1981 | Terada |
| 4,261,345 A | 4/1981 | Yamaguchi |

(Continued)

FOREIGN PATENT DOCUMENTS

| CN | 1988841 | 6/2007 |
| CN | 201108422 Y | 9/2008 |

(Continued)

OTHER PUBLICATIONS

International Search Report for PCT/EP2009/066726, Aug. 16, 2010.
(Continued)

*Primary Examiner* — Matthew J Kasztejna
(74) *Attorney, Agent, or Firm* — Novel IP

(57) ABSTRACT

There is provided herein a tip section of a multi-camera endoscope, the tip section comprising: a fluid channeling component for a tip section of a multi-camera endoscope, the fluid channeling component comprising one or more fluid channels configured for flowing for insufflation and/or irrigation fluid, and one or more support elements adapted to receive, support and/or secure a flexible electronic circuit board and/or one or more of a front camera, a side camera, an optical assembly, and a light source attached thereto; and a folded flexible electronic circuit board.

8 Claims, 7 Drawing Sheets

(51) Int. Cl.
*A61B 1/00* (2006.01)
*A61B 1/05* (2006.01)
*A61B 1/015* (2006.01)
*A61B 1/06* (2006.01)
*A61B 1/018* (2006.01)
*A61B 1/31* (2006.01)

(52) U.S. Cl.
CPC .. *A61B 1/04* (2013.01); *A61B 1/05* (2013.01); *A61B 1/0676* (2013.01); *A61B 1/0684* (2013.01); *A61B 1/018* (2013.01); *A61B 1/31* (2013.01)

(56) References Cited

U.S. PATENT DOCUMENTS

| | | |
|---|---|---|
| 4,402,313 A | 9/1983 | Yabe |
| 4,414,608 A | 11/1983 | Furihata |
| 4,439,030 A | 3/1984 | Ueda |
| 4,469,090 A | 9/1984 | Konomura |
| 4,494,549 A | 1/1985 | Namba |
| 4,522,196 A | 6/1985 | Cunningham |
| 4,565,423 A | 1/1986 | Ueda |
| 4,576,144 A | 3/1986 | Ishii |
| 4,588,294 A | 5/1986 | Siegmund |
| 4,590,923 A | 5/1986 | Watanabe |
| 4,641,635 A | 2/1987 | Yabe |
| 4,699,463 A | 10/1987 | D'Amelio et al. |
| 4,708,126 A | 11/1987 | Toda |
| 4,736,732 A | 4/1988 | Shimonaka |
| 4,753,222 A | 6/1988 | Morishita |
| 4,764,001 A | 8/1988 | Yokota |
| 4,794,913 A | 1/1989 | Shimonaka |
| 4,801,792 A | 1/1989 | Yamasita |
| 4,841,952 A | 6/1989 | Sato |
| 4,846,154 A | 7/1989 | MacAnally |
| 4,877,314 A | 10/1989 | Kanamori |
| 4,878,485 A | 11/1989 | Adair |
| 4,888,639 A | 12/1989 | Yabe |
| 4,902,115 A | 2/1990 | Takahashi |
| 4,905,670 A | 3/1990 | Adair |
| 4,914,521 A | 4/1990 | Adair |
| 4,974,075 A | 11/1990 | Nakajima |
| 4,976,522 A | 12/1990 | Igarashi |
| 4,982,724 A | 1/1991 | Saito |
| 4,984,878 A | 1/1991 | Miyano |
| 4,998,182 A | 3/1991 | Krauter |
| 5,166,787 A | 11/1992 | Irion |
| 5,193,525 A | 3/1993 | Silverstein |
| 5,239,983 A | 8/1993 | Katsurada |
| 5,296,971 A | 3/1994 | Mori |
| 5,299,561 A | 4/1994 | Yoshimoto |
| 5,305,121 A | 4/1994 | Moll |
| 5,309,227 A | 5/1994 | Inoue |
| 5,313,934 A | 5/1994 | Wiita |
| 5,339,800 A | 8/1994 | Wiita |
| 5,359,456 A | 10/1994 | Kikuchi |
| 5,380,049 A | 1/1995 | Smowton |
| 5,398,056 A | 3/1995 | Yabe |
| 5,408,623 A | 4/1995 | Dolidon |
| 5,412,478 A | 5/1995 | Ishihara |
| 5,420,644 A | 5/1995 | Watanabe |
| 5,432,543 A | 7/1995 | Hasegawa |
| 5,436,767 A | 7/1995 | Suzuki |
| 5,447,148 A | 9/1995 | Oneda |
| 5,452,391 A | 9/1995 | Chou |
| 5,460,167 A | 10/1995 | Yabe |
| 5,483,951 A | 1/1996 | Frassica |
| 5,485,316 A | 1/1996 | Mori |
| 5,489,256 A | 2/1996 | Adair |
| 5,507,717 A | 4/1996 | Kura |
| 5,512,940 A | 4/1996 | Takasugi |
| 5,515,449 A | 5/1996 | Tsuruoka |
| 5,518,501 A | 5/1996 | Oneda |
| 5,518,502 A | 5/1996 | Kaplan |
| 5,547,455 A | 8/1996 | McKenna |
| 5,547,457 A | 8/1996 | Tsuyuki |
| 5,550,582 A | 8/1996 | Takasugi |
| 5,585,840 A | 12/1996 | Watanabe |
| 5,587,839 A | 12/1996 | Miyano |
| 5,589,874 A | 12/1996 | Buchin |
| 5,592,216 A | 1/1997 | Uehara |
| 5,605,530 A | 2/1997 | Fischell |
| 5,609,560 A | 3/1997 | Ichikawa |
| 5,617,136 A | 4/1997 | Iso |
| 5,630,782 A | 5/1997 | Adair |
| 5,653,677 A | 8/1997 | Okada |
| 5,656,011 A | 8/1997 | Uihlein |
| 5,675,378 A | 10/1997 | Takasugi |
| 5,679,110 A | 10/1997 | Hamazaki |
| 5,685,823 A | 11/1997 | Ito |
| 5,701,155 A | 12/1997 | Wood |
| 5,702,345 A | 12/1997 | Wood |
| 5,702,347 A | 12/1997 | Yabe |
| 5,716,323 A | 2/1998 | Lee |
| 5,725,474 A | 3/1998 | Yasui |
| 5,725,476 A | 3/1998 | Yasui |
| 5,725,477 A | 3/1998 | Yasui |
| 5,728,045 A | 3/1998 | Komi |
| 5,751,340 A | 5/1998 | Strobl |
| 5,764,809 A | 6/1998 | Nomami |
| 5,777,797 A | 7/1998 | Miyano |
| 5,782,751 A | 7/1998 | Matsuno |
| 5,793,539 A | 8/1998 | Konno |
| 5,800,341 A | 9/1998 | McKenna |
| 5,812,187 A | 9/1998 | Watanabe |
| 5,830,124 A | 11/1998 | Suzuki |
| 5,852,511 A | 12/1998 | Tateyama |
| 5,870,234 A | 2/1999 | EbbesmeierneeSchitthof |
| 5,871,439 A | 2/1999 | Takahashi |
| 5,876,326 A | 3/1999 | Takamura |
| 5,879,284 A | 3/1999 | Tsujita |
| 5,894,322 A | 4/1999 | Hamano |
| 5,912,764 A | 6/1999 | Togino |
| 5,913,817 A | 6/1999 | Lee |
| 5,914,810 A | 6/1999 | Watts |
| 5,916,148 A | 6/1999 | Tsuyuki |
| 5,929,901 A | 7/1999 | Adair |
| 5,930,424 A | 7/1999 | Heimberger |
| 5,933,275 A | 8/1999 | Igarashi |
| 5,933,282 A | 8/1999 | Tomioka |
| 5,936,773 A | 8/1999 | Togino |
| 5,940,126 A | 8/1999 | Kimura |
| 5,961,445 A | 10/1999 | Chikama |
| 5,969,888 A | 10/1999 | Sukekawa |
| 5,986,693 A | 11/1999 | Adair |
| 5,989,185 A | 11/1999 | Miyazaki |
| 5,993,037 A | 11/1999 | Tomioka |
| 5,995,136 A | 11/1999 | Hattori |
| 6,009,189 A | 12/1999 | Schaack |
| 6,043,839 A | 3/2000 | Adair |
| 6,069,698 A | 5/2000 | Ozawa |
| 6,080,104 A | 6/2000 | Ozawa |
| 6,104,540 A | 8/2000 | Hayakawa |
| 6,110,127 A | 8/2000 | Suzuki |
| 6,124,989 A | 9/2000 | Oode |
| 6,139,175 A | 10/2000 | Tomioka |
| 6,139,490 A | 10/2000 | Breidenthal |
| 6,147,808 A | 11/2000 | Togino |
| 6,163,401 A | 12/2000 | Igarashi |
| 6,166,858 A | 12/2000 | Togino |
| 6,181,481 B1 | 1/2001 | Yamamoto |
| 6,184,923 B1 | 2/2001 | Miyazaki |
| 6,185,046 B1 | 2/2001 | Togino |
| 6,201,646 B1 | 3/2001 | Togino |
| 6,201,648 B1 | 3/2001 | Togino |
| 6,211,904 B1 | 4/2001 | Adair |
| 6,215,517 B1 | 4/2001 | Takahashi |
| 6,217,500 B1 | 4/2001 | Helseth |
| 6,245,086 B1 | 6/2001 | Storz |
| 6,249,391 B1 | 6/2001 | Hayakawa |
| 6,260,994 B1 | 7/2001 | Matsumoto |
| 6,261,226 B1 | 7/2001 | McKenna |
| 6,275,255 B1 | 8/2001 | Adair |

(56) References Cited

U.S. PATENT DOCUMENTS

| | | |
|---|---|---|
| 6,295,368 B1 | 9/2001 | Hasegawa |
| 6,306,082 B1 | 10/2001 | Takahashi |
| 6,310,642 B1 | 10/2001 | Adair |
| 6,310,736 B1 | 10/2001 | Togino |
| 6,315,712 B1 | 11/2001 | Rovegno |
| 6,322,496 B1 | 11/2001 | Iida |
| 6,327,094 B1 | 12/2001 | Aoki |
| 6,327,101 B1 | 12/2001 | Miyano |
| 6,334,845 B1 | 1/2002 | Higuchi |
| 6,353,504 B1 | 3/2002 | Yamamoto |
| 6,387,045 B1 | 5/2002 | Takahashi |
| 6,398,723 B1 | 6/2002 | Kehr |
| 6,400,514 B2 | 6/2002 | Minami |
| 6,422,995 B2 | 7/2002 | Akiba |
| 6,425,857 B1 | 7/2002 | Rudischhauser |
| 6,450,950 B2 | 9/2002 | Irion |
| 6,461,304 B1 | 10/2002 | Tanaka |
| 6,464,631 B1 | 10/2002 | Girke |
| 6,464,633 B1 | 10/2002 | Hosoda |
| 6,468,201 B1 | 10/2002 | Burdick |
| 6,468,202 B1 | 10/2002 | Irion |
| 6,471,636 B1 | 10/2002 | Sano |
| 6,471,637 B1 | 10/2002 | Green |
| 6,473,116 B1 | 10/2002 | Takahashi |
| 6,476,851 B1 | 11/2002 | Nakamura |
| 6,500,115 B2 | 12/2002 | Krattiger |
| 6,514,210 B2 | 2/2003 | Ohara |
| 6,520,908 B1 | 2/2003 | Ikeda |
| 6,527,704 B1 | 3/2003 | Chang |
| 6,530,881 B1 | 3/2003 | Ailinger |
| 6,533,722 B2 | 3/2003 | Nakashima |
| 6,545,703 B1 | 4/2003 | Takahashi |
| 6,551,239 B2 | 4/2003 | Renner |
| 6,554,767 B2 | 4/2003 | Tanaka |
| 6,567,114 B2 | 5/2003 | Takahashi |
| 6,569,084 B1 | 5/2003 | Mizuno |
| 6,582,361 B2 | 6/2003 | Hirano |
| 6,589,168 B2 | 7/2003 | Thompson |
| 6,606,113 B2 | 8/2003 | Nakamura |
| 6,618,205 B2 | 9/2003 | Murayama |
| D481,125 S | 10/2003 | Hayamizu |
| 6,638,212 B1 | 10/2003 | Oshima |
| 6,638,214 B2 | 10/2003 | Akiba |
| 6,641,531 B2 | 11/2003 | Kehr |
| 6,656,111 B2 | 12/2003 | Fujii |
| 6,671,099 B2 | 12/2003 | Nagata |
| 6,677,983 B1 | 1/2004 | Takahashi |
| 6,677,984 B2 | 1/2004 | Kobayashi |
| 6,677,992 B1 | 1/2004 | Matsumoto |
| 6,692,430 B2 | 2/2004 | Adler |
| 6,692,431 B2 | 2/2004 | Kazakevich |
| 6,699,181 B2 | 3/2004 | Wako |
| 6,699,185 B2 | 3/2004 | Gminder |
| 6,704,052 B1 | 3/2004 | Togino |
| 6,712,760 B2 | 3/2004 | Sano |
| D490,898 S | 6/2004 | Hayamizu |
| 6,764,439 B2 | 7/2004 | Schaaf |
| 6,778,208 B2 | 8/2004 | Takeshige |
| 6,788,343 B1 | 9/2004 | Togino |
| 6,793,621 B2 | 9/2004 | Butler |
| 6,801,325 B2 | 10/2004 | Farr |
| 6,809,499 B2 | 10/2004 | Solingen |
| 6,809,866 B2 | 10/2004 | Xie |
| 6,829,003 B2 | 12/2004 | Takami |
| 6,832,984 B2 | 12/2004 | Stelzer |
| 6,844,985 B2 | 1/2005 | Murayama |
| 6,846,311 B2 | 1/2005 | Gatto |
| 6,849,043 B2 | 2/2005 | Kondo |
| 6,860,516 B2 | 3/2005 | Ouchi |
| 6,876,380 B2 | 4/2005 | Abe |
| 6,887,194 B2 | 5/2005 | Hart |
| 6,888,119 B2 | 5/2005 | Iizuka |
| 6,898,086 B2 | 5/2005 | Takami |
| 6,899,673 B2 | 5/2005 | Ogura |
| 6,900,829 B1 | 5/2005 | Ozawa |
| 6,900,950 B2 | 5/2005 | Nagata |
| 6,902,529 B2 | 6/2005 | Onishi |
| 6,903,761 B1 | 6/2005 | Abe |
| 6,918,693 B2 | 7/2005 | Ota |
| 6,921,362 B2 | 7/2005 | Ouchi |
| 6,930,705 B2 | 8/2005 | Tanaka |
| 6,933,962 B2 | 8/2005 | Yamamoto |
| 6,937,267 B1 | 8/2005 | Takahashi |
| 6,937,269 B2 | 8/2005 | Sugimoto |
| 6,943,821 B2 | 9/2005 | Abe |
| 6,943,822 B2 | 9/2005 | Iida |
| 6,944,031 B2 | 9/2005 | Takami |
| 6,945,929 B2 | 9/2005 | Ando |
| 6,947,070 B2 | 9/2005 | Takami |
| 6,950,691 B2 | 9/2005 | Uchikubo |
| 6,956,703 B2 | 10/2005 | Saito |
| 6,967,673 B2 | 11/2005 | Ozawa |
| 6,977,670 B2 | 12/2005 | Takahashi |
| 6,980,227 B2 | 12/2005 | Iida |
| 6,982,740 B2 | 1/2006 | Adair |
| 6,985,170 B1 | 1/2006 | Tsuyuki |
| 6,992,694 B2 | 1/2006 | Abe |
| 6,995,786 B2 | 2/2006 | Abe |
| 6,997,871 B2 | 2/2006 | Sonnenschein |
| 7,027,231 B2 | 4/2006 | Miyano |
| 7,030,904 B2 | 4/2006 | Adair |
| 7,037,258 B2 | 5/2006 | Chatenever |
| 7,042,488 B2 | 5/2006 | Higuchi |
| 7,043,153 B2 | 5/2006 | Takeyama |
| 7,046,270 B2 | 5/2006 | Murata |
| 7,050,086 B2 | 5/2006 | Ozawa |
| 7,074,181 B2 | 7/2006 | Futatsugi |
| 7,074,182 B2 | 7/2006 | Rovegno |
| 7,085,064 B2 | 8/2006 | Uzawa |
| 7,097,615 B2 | 8/2006 | Banik |
| 7,104,951 B2 | 9/2006 | Hasegawa |
| 7,108,656 B2 | 9/2006 | Fujikawa |
| 7,108,657 B2 | 9/2006 | Irion |
| 7,119,830 B2 | 10/2006 | Saito |
| 7,123,288 B2 | 10/2006 | Abe |
| 7,128,709 B2 | 10/2006 | Saruya |
| 7,129,472 B1 | 10/2006 | Okawa |
| 7,133,063 B2 | 11/2006 | Abe |
| D534,656 S | 1/2007 | Pilvisto |
| 7,156,863 B2 | 1/2007 | Sonnenschein |
| 7,158,314 B2 | 1/2007 | Fujii |
| 7,179,221 B2 | 2/2007 | Tsujita |
| 7,180,686 B2 | 2/2007 | Kato |
| 7,218,454 B2 | 5/2007 | Miyano |
| 7,223,231 B2 | 5/2007 | Akiba |
| 7,231,135 B2 | 6/2007 | Esenyan |
| 7,232,409 B2 | 6/2007 | Hale |
| 7,233,820 B2 | 6/2007 | Gilboa |
| 7,242,833 B2 | 7/2007 | Yang |
| 7,248,281 B2 | 7/2007 | Abe |
| 7,248,296 B2 | 7/2007 | Iketani |
| 7,252,633 B2 | 8/2007 | Obata |
| 7,255,676 B2 | 8/2007 | Higuchi |
| 7,262,797 B2 | 8/2007 | Weldum |
| 7,267,647 B2 | 9/2007 | Okada |
| 7,273,452 B2 | 9/2007 | Barbato |
| 7,277,120 B2 | 10/2007 | Gere |
| 7,280,140 B2 | 10/2007 | Henderson |
| 7,280,283 B1 | 10/2007 | Kasai |
| 7,282,025 B2 | 10/2007 | Abe |
| 7,306,588 B2 | 12/2007 | Loeb |
| 7,330,749 B1 | 2/2008 | Bhunachet |
| D564,659 S | 3/2008 | Hayashi |
| D564,660 S | 3/2008 | Hayashi |
| 7,351,202 B2 | 4/2008 | Long |
| 7,355,625 B1 | 4/2008 | Mochida |
| 7,358,987 B2 | 4/2008 | Takeshige |
| 7,365,768 B1 | 4/2008 | Ono |
| 7,371,211 B2 | 5/2008 | Akiba |
| 7,379,252 B2 | 5/2008 | Murayama |
| 7,384,308 B2 | 6/2008 | Boehnlein |
| 7,399,304 B2 | 7/2008 | Gambale |
| 7,400,341 B2 | 7/2008 | Abe |
| 7,401,984 B2 | 7/2008 | Pattie |

(56) References Cited

U.S. PATENT DOCUMENTS

| | | |
|---|---|---|
| 7,409,130 B2 | 8/2008 | Hatori |
| 7,420,586 B2 | 9/2008 | Higuchi |
| 7,427,263 B2 | 9/2008 | Hoeg |
| 7,431,619 B2 | 10/2008 | Boehnlein |
| 7,435,217 B2 | 10/2008 | Wiklof |
| 7,435,218 B2 | 10/2008 | Krattiger |
| 7,440,005 B2 | 10/2008 | Enomoto |
| 7,443,488 B2 | 10/2008 | Ogawa |
| 7,450,151 B2 | 11/2008 | Kaneko |
| 7,466,490 B2 | 12/2008 | Igarashi |
| 7,471,310 B2 | 12/2008 | Amling |
| 7,484,709 B2 | 2/2009 | Efinger |
| 7,486,449 B2 | 2/2009 | Miyano |
| 7,492,388 B2 | 2/2009 | Odlivak |
| 7,514,667 B2 | 4/2009 | Matsumoto |
| 7,518,632 B2 | 4/2009 | Konomura |
| 7,530,948 B2 | 5/2009 | Seibel |
| 7,542,069 B2 | 6/2009 | Tashiro |
| 7,553,276 B2 | 6/2009 | Iddan |
| 7,559,889 B2 | 7/2009 | Takahashi |
| 7,559,892 B2 | 7/2009 | Adler |
| 7,561,351 B2 | 7/2009 | Konno |
| 7,569,012 B2 | 8/2009 | Tanaka |
| 7,573,499 B2 | 8/2009 | Doguchi |
| 7,576,310 B2 | 8/2009 | Konno |
| 7,581,988 B2 | 9/2009 | Boehnlein |
| 7,582,055 B2 | 9/2009 | Komiya |
| 7,582,056 B2 | 9/2009 | Noguchi |
| 7,584,534 B2 | 9/2009 | Pease |
| 7,585,274 B2 | 9/2009 | Homma |
| 7,588,535 B2 | 9/2009 | Adler |
| 7,593,051 B2 | 9/2009 | Suda |
| 7,621,868 B2 | 11/2009 | Breidenthal |
| 7,621,869 B2 | 11/2009 | Ratnakar |
| 7,623,150 B2 | 11/2009 | Kobayashi |
| 7,627,189 B2 | 12/2009 | Donomae |
| 7,630,148 B1 | 12/2009 | Yang |
| 7,671,888 B2 | 3/2010 | Nogami |
| 7,683,927 B2 | 3/2010 | Higuchi |
| 7,695,429 B2 | 4/2010 | Hino |
| 7,699,772 B2 | 4/2010 | Pauker |
| 7,701,650 B2 | 4/2010 | Lin |
| 7,725,013 B2 | 5/2010 | Sugimoto |
| 7,728,867 B2 | 6/2010 | Fukuyama |
| 7,734,160 B2 | 6/2010 | Sudo |
| 7,746,566 B2 | 6/2010 | Mizusawa |
| 7,746,572 B2 | 6/2010 | Asami |
| 7,749,156 B2 | 7/2010 | Ouchi |
| 7,749,159 B2 | 7/2010 | Crowley |
| 7,758,495 B2 | 7/2010 | Pease |
| 7,758,499 B2 | 7/2010 | Adler |
| 7,772,786 B2 | 8/2010 | Hosoda |
| 7,773,110 B2 | 8/2010 | Abe |
| 7,773,122 B2 | 8/2010 | Irion |
| 7,773,318 B2 | 8/2010 | Takato |
| 7,775,971 B2 | 8/2010 | Fujimori |
| 7,775,973 B2 | 8/2010 | Okada |
| 7,789,822 B2 | 9/2010 | Suzuki |
| 7,800,656 B2 | 9/2010 | Takeuchi |
| RE41,807 E | 10/2010 | Yokoi |
| 7,821,529 B2 | 10/2010 | Mochida |
| 7,837,614 B2 | 11/2010 | Segawa |
| 7,841,880 B2 | 11/2010 | Ikeda |
| 7,846,090 B2 | 12/2010 | Pilvisto |
| 7,852,513 B2 | 12/2010 | Donomae |
| 7,893,956 B2 | 2/2011 | Ayrenschmalz |
| 7,896,802 B2 | 3/2011 | Otawara |
| 7,901,352 B2 | 3/2011 | Minami |
| 7,907,168 B2 | 3/2011 | Eino |
| 7,907,170 B2 | 3/2011 | Watanabe |
| 7,907,352 B2 | 3/2011 | Miyano |
| 7,914,443 B2 | 3/2011 | Uchimura |
| 7,918,788 B2 | 4/2011 | Lin |
| 7,938,773 B2 | 5/2011 | Kawai |
| 7,940,296 B2 | 5/2011 | Ogino |
| 7,942,814 B2 | 5/2011 | Remijan |
| 7,951,068 B2 | 5/2011 | Kura |
| 7,967,745 B2 | 6/2011 | Gilad |
| 7,976,462 B2 | 7/2011 | Wright |
| 7,995,093 B2 | 8/2011 | Takeuchi |
| 7,998,064 B2 | 8/2011 | Otawara |
| 8,002,696 B2 | 8/2011 | Suzuki |
| 8,027,101 B2 | 9/2011 | Suda |
| 8,033,992 B2 | 10/2011 | Hino |
| 8,035,684 B2 | 10/2011 | Wakito |
| 8,038,600 B2 | 10/2011 | Uchiyama |
| 8,043,207 B2 | 10/2011 | Adams |
| 8,060,172 B2 | 11/2011 | Ishihara |
| 8,063,962 B2 | 11/2011 | Hagihara |
| 8,066,631 B2 | 11/2011 | Wimmer |
| 8,072,483 B2 | 12/2011 | Tomioka |
| 8,072,537 B2 | 12/2011 | Schwarz |
| 8,072,693 B2 | 12/2011 | Togino |
| 8,075,477 B2 | 12/2011 | Nakamura |
| 8,075,478 B2 | 12/2011 | Campos |
| 8,098,441 B2 | 1/2012 | Sasamoto |
| 8,100,920 B2 | 1/2012 | Gambale |
| 8,102,415 B2 | 1/2012 | Iriyama |
| 8,105,233 B2 | 1/2012 | AbouElKheir |
| 8,113,846 B2 | 2/2012 | Wallaker |
| 8,125,514 B2 | 2/2012 | Sekiguchi |
| 8,125,515 B2 | 2/2012 | Hibi |
| 8,130,454 B2 | 3/2012 | Noguchi |
| 8,135,192 B2 | 3/2012 | Matsuzaki |
| 8,135,454 B2 | 3/2012 | Daniels |
| 8,139,296 B2 | 3/2012 | Ito |
| 8,144,191 B2 | 3/2012 | Kawanishi |
| 8,149,274 B2 | 4/2012 | Yamazaki |
| 8,152,718 B2 | 4/2012 | Cheng |
| 8,152,821 B2 | 4/2012 | Gambale |
| 8,157,798 B2 | 4/2012 | Takahashi |
| 8,164,836 B2 | 4/2012 | Uzawa |
| 8,167,791 B2 | 5/2012 | Tanaka |
| 8,167,795 B2 | 5/2012 | Hoeg |
| 8,167,796 B2 | 5/2012 | Negishi |
| 8,182,419 B2 | 5/2012 | Kohno |
| 8,187,171 B2 | 5/2012 | Irion |
| 8,187,174 B2 | 5/2012 | Wang |
| 8,189,041 B2 | 5/2012 | Konishi |
| 8,189,062 B2 | 5/2012 | Irion |
| 8,194,380 B2 | 6/2012 | Murata |
| 8,197,400 B2 | 6/2012 | Boutillette |
| 8,200,042 B2 | 6/2012 | Doi |
| 8,208,015 B2 | 6/2012 | Unsai |
| 8,211,009 B2 | 7/2012 | Tanaka |
| 8,212,862 B2 | 7/2012 | Kase |
| 8,212,863 B2 | 7/2012 | Tanaka |
| 8,221,309 B2 | 7/2012 | Iida |
| 8,221,311 B2 | 7/2012 | Campos |
| 8,223,198 B2 | 7/2012 | Shibasaki |
| 8,228,369 B2 | 7/2012 | Kojima |
| 8,229,549 B2 | 7/2012 | Whitman |
| 8,235,942 B2 | 8/2012 | Frassica |
| 8,248,414 B2 | 8/2012 | Gattani |
| 8,262,565 B2 | 9/2012 | Okada |
| 8,279,275 B2 | 10/2012 | Gono |
| 8,295,566 B2 | 10/2012 | Nishimura |
| 8,300,325 B2 | 10/2012 | Katahira |
| 8,310,529 B2 | 11/2012 | Krupnick |
| 8,334,900 B2 | 12/2012 | Qu |
| 8,345,092 B2 | 1/2013 | Takasaki |
| 8,348,835 B2 | 1/2013 | Fujimori |
| 8,360,960 B2 | 1/2013 | Sasaki |
| 8,360,964 B2 | 1/2013 | Ertas |
| 8,366,623 B2 | 2/2013 | Misono |
| 8,382,673 B2 | 2/2013 | Nagano |
| 8,394,013 B2 | 3/2013 | Ichimura |
| 8,394,014 B2 | 3/2013 | Fuerst |
| 8,425,405 B2 | 4/2013 | Mitani |
| 8,435,173 B2 | 5/2013 | Hosaka |
| 8,439,829 B2 | 5/2013 | Miyamoto |
| 8,444,547 B2 | 5/2013 | Miyamoto |
| 8,444,548 B2 | 5/2013 | Kumei |
| 8,449,456 B2 | 5/2013 | Ueno |

(56) References Cited

U.S. PATENT DOCUMENTS

| | | | |
|---|---|---|---|
| 8,449,457 B2 | 5/2013 | Aizenfeld | |
| 8,456,562 B2 | 6/2013 | Ishii | |
| 8,460,182 B2 | 6/2013 | Ouyang | |
| 8,465,421 B2 | 6/2013 | Finkman | |
| 8,480,670 B2 | 7/2013 | Sugita | |
| 8,491,467 B2 | 7/2013 | Miyamoto | |
| 8,520,919 B2 | 8/2013 | Stepp | |
| 8,523,764 B2 | 9/2013 | Hatcher | |
| 8,523,766 B2 | 9/2013 | Kudoh | |
| 2002/0007110 A1 | 1/2002 | Irion | |
| 2002/0087047 A1 | 7/2002 | Remijan | |
| 2002/0098732 A1 | 7/2002 | Shimizu | |
| 2002/0109774 A1 | 8/2002 | Meron | |
| 2002/0151768 A1 | 10/2002 | Akiba | |
| 2002/0161281 A1 | 10/2002 | Jaffe | |
| 2002/0161282 A1 | 10/2002 | Fulghum | |
| 2002/0183591 A1 | 12/2002 | Matsuura | |
| 2003/0030918 A1 | 2/2003 | Murayama | |
| 2003/0032860 A1 | 2/2003 | Avni | |
| 2003/0036681 A1 | 2/2003 | Aviv | |
| 2003/0055314 A1 | 3/2003 | Petitto | |
| 2003/0083552 A1 | 5/2003 | Remijan | |
| 2003/0125788 A1 | 7/2003 | Long | |
| 2003/0130564 A1 | 7/2003 | Martone | |
| 2003/0139648 A1 | 7/2003 | Foley | |
| 2003/0158462 A1 | 8/2003 | Takase | |
| 2003/0181787 A1 | 9/2003 | Kondo | |
| 2003/0199860 A1 | 10/2003 | Loeb | |
| 2004/0015049 A1 | 1/2004 | Zaar | |
| 2004/0019347 A1 | 1/2004 | Sakurai | |
| 2004/0024290 A1 | 2/2004 | Root | |
| 2004/0034311 A1 | 2/2004 | Mihalcik | |
| 2004/0073120 A1 | 4/2004 | Motz | |
| 2004/0104999 A1 | 6/2004 | Okada | |
| 2004/0111012 A1 | 6/2004 | Whitman | |
| 2004/0133076 A1 | 7/2004 | Kobayashi | |
| 2004/0138532 A1 | 7/2004 | Glukhovsky | |
| 2004/0143162 A1 | 7/2004 | Krattiger | |
| 2004/0158129 A1 | 8/2004 | Okada | |
| 2004/0160682 A1 | 8/2004 | Miyano | |
| 2004/0176661 A1 | 9/2004 | Futatsugi | |
| 2004/0190159 A1 | 9/2004 | Hasegawa | |
| 2004/0210113 A1 | 10/2004 | Hasegawa | |
| 2004/0220451 A1 | 11/2004 | Gravenstein | |
| 2004/0242958 A1 | 12/2004 | Fujikawa | |
| 2004/0242961 A1 | 12/2004 | Bughici | |
| 2004/0254423 A1 | 12/2004 | Wendlandt | |
| 2004/0267093 A1 | 12/2004 | Miyagi | |
| 2005/0020876 A1 | 1/2005 | Shioda | |
| 2005/0027164 A1 | 2/2005 | Barbato | |
| 2005/0038317 A1 | 2/2005 | Ratnakar | |
| 2005/0038318 A1 | 2/2005 | Goldwasser | |
| 2005/0043583 A1 | 2/2005 | Killmann | |
| 2005/0080342 A1 | 4/2005 | Gilreath | |
| 2005/0090709 A1 | 4/2005 | Okada | |
| 2005/0096501 A1 | 5/2005 | Stelzer | |
| 2005/0154255 A1 | 7/2005 | Jacobs | |
| 2005/0154262 A1 | 7/2005 | Banik | |
| 2005/0182295 A1 | 8/2005 | Soper | |
| 2005/0203338 A1 | 9/2005 | Couvillon | |
| 2005/0234296 A1 | 10/2005 | Saadat | |
| 2005/0234347 A1 | 10/2005 | Yamataka | |
| 2005/0251127 A1 | 11/2005 | Brosch | |
| 2005/0261553 A1 | 11/2005 | Swain | |
| 2005/0272975 A1 | 12/2005 | McWeeney | |
| 2005/0283048 A1 | 12/2005 | Gill | |
| 2005/0284491 A1 | 12/2005 | Tashiro | |
| 2006/0047184 A1 | 3/2006 | Banik | |
| 2006/0052663 A1 | 3/2006 | Koitabashi | |
| 2006/0063976 A1 | 3/2006 | Aizenfeld | |
| 2006/0069307 A1 | 3/2006 | Boulais | |
| 2006/0069314 A1 | 3/2006 | Farr | |
| 2006/0149129 A1 | 7/2006 | Watts | |
| 2006/0173244 A1 | 8/2006 | Boulais | |
| 2006/0183971 A1 | 8/2006 | Haviv | |
| 2006/0183975 A1 | 8/2006 | Saadat | |
| 2006/0189845 A1 | 8/2006 | Maahs | |
| 2006/0211916 A1 | 9/2006 | Kasahara | |
| 2006/0217594 A1 | 9/2006 | Ferguson | |
| 2006/0224040 A1 | 10/2006 | Khait | |
| 2006/0229499 A1 | 10/2006 | Eisenkolb | |
| 2006/0241347 A1 | 10/2006 | Whitehead | |
| 2006/0252994 A1* | 11/2006 | Ratnakar | 600/173 |
| 2006/0264704 A1 | 11/2006 | Fujimori | |
| 2006/0293556 A1 | 12/2006 | Garner | |
| 2006/0293562 A1 | 12/2006 | Uchimura | |
| 2007/0015964 A1 | 1/2007 | Eversull | |
| 2007/0015968 A1 | 1/2007 | Shelnutt | |
| 2007/0019916 A1 | 1/2007 | Takami | |
| 2007/0049803 A1 | 3/2007 | Moriyama | |
| 2007/0055100 A1 | 3/2007 | Kato | |
| 2007/0073109 A1 | 3/2007 | Irion | |
| 2007/0078304 A1 | 4/2007 | Shimizu | |
| 2007/0083081 A1 | 4/2007 | Schlagenhauf | |
| 2007/0100206 A1 | 5/2007 | Lin | |
| 2007/0106119 A1 | 5/2007 | Hirata | |
| 2007/0115376 A1 | 5/2007 | Igarashi | |
| 2007/0118019 A1 | 5/2007 | Mitani | |
| 2007/0123748 A1 | 5/2007 | Meglan | |
| 2007/0142711 A1 | 6/2007 | Bayer | |
| 2007/0162095 A1 | 7/2007 | Kimmel | |
| 2007/0167673 A1 | 7/2007 | Enomoto | |
| 2007/0167681 A1 | 7/2007 | Gill | |
| 2007/0173686 A1 | 7/2007 | Lin | |
| 2007/0173687 A1 | 7/2007 | Shima | |
| 2007/0177008 A1 | 8/2007 | Bayer | |
| 2007/0177009 A1 | 8/2007 | Bayer | |
| 2007/0185384 A1 | 8/2007 | Bayer | |
| 2007/0197875 A1 | 8/2007 | Osaka | |
| 2007/0203396 A1 | 8/2007 | McCutcheon | |
| 2007/0206945 A1 | 9/2007 | DeLorme | |
| 2007/0208225 A1 | 9/2007 | Czaniera | |
| 2007/0213590 A1 | 9/2007 | Squicciarini | |
| 2007/0213591 A1 | 9/2007 | Aizenfeld | |
| 2007/0225556 A1 | 9/2007 | Ortiz | |
| 2007/0225565 A1 | 9/2007 | Ogino | |
| 2007/0229656 A1 | 10/2007 | Khait | |
| 2007/0244353 A1 | 10/2007 | Larsen | |
| 2007/0244362 A1 | 10/2007 | El-Hachem | |
| 2007/0244366 A1 | 10/2007 | Murata | |
| 2007/0249899 A1 | 10/2007 | Seifert | |
| 2007/0265498 A1 | 11/2007 | Ito | |
| 2007/0282165 A1 | 12/2007 | Hopkins | |
| 2007/0293720 A1 | 12/2007 | Bayer | |
| 2008/0009672 A1 | 1/2008 | Krattiger | |
| 2008/0021274 A1 | 1/2008 | Bayer | |
| 2008/0021281 A1 | 1/2008 | Fujimori | |
| 2008/0039689 A1 | 2/2008 | Yoshimitsu | |
| 2008/0039693 A1 | 2/2008 | Karasawa | |
| 2008/0045797 A1 | 2/2008 | Yasushi | |
| 2008/0051628 A1 | 2/2008 | Pecherer | |
| 2008/0051629 A1 | 2/2008 | Sugiyama | |
| 2008/0051655 A1 | 2/2008 | Sato | |
| 2008/0058595 A1 | 3/2008 | Snoke | |
| 2008/0058598 A1 | 3/2008 | Ries | |
| 2008/0058601 A1 | 3/2008 | Fujimori | |
| 2008/0064931 A1 | 3/2008 | Schena | |
| 2008/0065127 A1 | 3/2008 | Adams | |
| 2008/0071290 A1 | 3/2008 | Larkin | |
| 2008/0100699 A1 | 5/2008 | Hibi | |
| 2008/0130108 A1 | 6/2008 | Bayer | |
| 2008/0139881 A1 | 6/2008 | Cover | |
| 2008/0167529 A1 | 7/2008 | Otawara | |
| 2008/0171910 A1 | 7/2008 | Kanazawa | |
| 2008/0177139 A1 | 7/2008 | Courtney | |
| 2008/0177140 A1 | 7/2008 | Cline | |
| 2008/0188715 A1 | 8/2008 | Fujimoto | |
| 2008/0225134 A1 | 9/2008 | Amling | |
| 2008/0255425 A1 | 10/2008 | Voegele | |
| 2008/0262302 A1 | 10/2008 | Azarbarzin | |
| 2008/0262312 A1 | 10/2008 | Carroll | |
| 2008/0312497 A1 | 12/2008 | Elmouelhi | |
| 2009/0054790 A1 | 2/2009 | Czaniera | |
| 2009/0062615 A1 | 3/2009 | Yamaya | |

(56) References Cited

U.S. PATENT DOCUMENTS

| | | |
|---|---|---|
| 2009/0086017 A1 | 4/2009 | Miyano |
| 2009/0093679 A1 | 4/2009 | Suigetsu |
| 2009/0118577 A9 | 5/2009 | Snay |
| 2009/0137869 A1 | 5/2009 | Soutorine |
| 2009/0147076 A1 | 6/2009 | Ertas |
| 2009/0163769 A1 | 6/2009 | Robertson |
| 2009/0209811 A1 | 8/2009 | Higuchi |
| 2009/0216084 A1 | 8/2009 | Yamane |
| 2009/0231419 A1 | 9/2009 | Bayer |
| 2009/0247831 A1 | 10/2009 | Miyamoto |
| 2009/0253966 A1 | 10/2009 | Ichimura |
| 2009/0259097 A1 | 10/2009 | Thompson |
| 2009/0259102 A1 | 10/2009 | Koninckx |
| 2009/0268011 A1 | 10/2009 | Scott |
| 2009/0284649 A1 | 11/2009 | Pease |
| 2009/0287047 A1 | 11/2009 | Onoda |
| 2009/0287192 A1 | 11/2009 | Vivenzio |
| 2009/0306474 A1 | 12/2009 | Wilson |
| 2009/0306476 A1 | 12/2009 | Banik |
| 2009/0318757 A1 | 12/2009 | Singh |
| 2010/0010301 A1 | 1/2010 | Hale |
| 2010/0010302 A1 | 1/2010 | Hadani |
| 2010/0016673 A1 | 1/2010 | Bandy |
| 2010/0030020 A1 | 2/2010 | Sanders |
| 2010/0042097 A1 | 2/2010 | Newton |
| 2010/0047733 A1 | 2/2010 | Nahlieli |
| 2010/0053312 A1 | 3/2010 | Watanabe |
| 2010/0073470 A1 | 3/2010 | Takasaki |
| 2010/0076268 A1 | 3/2010 | Takasugi |
| 2010/0081874 A1 | 4/2010 | Miyamoto |
| 2010/0081875 A1 | 4/2010 | Fowler |
| 2010/0087706 A1 | 4/2010 | Syed |
| 2010/0121142 A1 | 5/2010 | Ouyang |
| 2010/0123950 A1 | 5/2010 | Fujiwara |
| 2010/0130822 A1 | 5/2010 | Katayama |
| 2010/0137682 A1 | 6/2010 | Doguchi |
| 2010/0137687 A1 | 6/2010 | Schwartz |
| 2010/0141746 A1 | 6/2010 | Ikeda |
| 2010/0152612 A1 | 6/2010 | Headley |
| 2010/0160729 A1 | 6/2010 | Smith |
| 2010/0174144 A1 | 7/2010 | Hsu |
| 2010/0185056 A1 | 7/2010 | Gordon |
| 2010/0187408 A1 | 7/2010 | Klem |
| 2010/0201985 A1 | 8/2010 | Wang |
| 2010/0204609 A1 | 8/2010 | Worth |
| 2010/0217076 A1 | 8/2010 | Ratnakar |
| 2010/0217081 A1 | 8/2010 | Deppmeier |
| 2010/0228086 A1 | 9/2010 | Ohki |
| 2010/0245653 A1 | 9/2010 | Bodor |
| 2010/0249496 A1 | 9/2010 | Cardenas |
| 2010/0256447 A1 | 10/2010 | Dubi |
| 2010/0286475 A1 | 11/2010 | Robertson |
| 2010/0296178 A1 | 11/2010 | Genet |
| 2010/0298640 A1 | 11/2010 | Oneda |
| 2010/0298773 A1 | 11/2010 | Nitsan |
| 2010/0305503 A1 | 12/2010 | Fang |
| 2010/0317919 A1 | 12/2010 | Takaoka |
| 2010/0317921 A1 | 12/2010 | Marple |
| 2010/0318061 A1 | 12/2010 | Derrick |
| 2011/0028790 A1 | 2/2011 | Farr |
| 2011/0054256 A1 | 3/2011 | Cushner |
| 2011/0112363 A1 | 5/2011 | Koga |
| 2011/0160530 A1 | 6/2011 | Ratnakar |
| 2011/0169931 A1 | 7/2011 | Pascal |
| 2011/0184243 A1 | 7/2011 | Wright |
| 2011/0196200 A1 | 8/2011 | Glozman |
| 2011/0196204 A1 | 8/2011 | Setty |
| 2011/0211267 A1 | 9/2011 | Takato |
| 2011/0224487 A1 | 9/2011 | Ogawa |
| 2011/0245600 A1 | 10/2011 | Ishii |
| 2011/0245609 A1 | 10/2011 | Laser |
| 2011/0257478 A1 | 10/2011 | Kleiner |
| 2011/0263938 A1 | 10/2011 | Levy |
| 2011/0282144 A1 | 11/2011 | Gettman |
| 2011/0282148 A1 | 11/2011 | Kase |
| 2011/0288374 A1 | 11/2011 | Hadani |
| 2011/0295061 A1 | 12/2011 | Haramaty |
| 2011/0295062 A1 | 12/2011 | GratacosSolsona |
| 2011/0295064 A1 | 12/2011 | Kagawa |
| 2011/0306832 A1 | 12/2011 | Bassan |
| 2011/0313249 A1 | 12/2011 | Viola |
| 2012/0010465 A1 | 1/2012 | Erikawa |
| 2012/0029291 A1 | 2/2012 | Wallace |
| 2012/0040305 A1 | 2/2012 | Karazivan |
| 2012/0041534 A1 | 2/2012 | Clerc |
| 2012/0046524 A1 | 2/2012 | Miyamoto |
| 2012/0053407 A1 | 3/2012 | Levy |
| 2012/0057251 A1 | 3/2012 | Takato |
| 2012/0065468 A1 | 3/2012 | Levy |
| 2012/0071748 A1 | 3/2012 | Mark |
| 2012/0078042 A1 | 3/2012 | Uram |
| 2012/0088965 A1 | 4/2012 | Stokes |
| 2012/0095391 A1 | 4/2012 | Bendele |
| 2012/0104230 A1 | 5/2012 | Eismann |
| 2012/0178995 A1 | 7/2012 | Newton |
| 2012/0209062 A1 | 8/2012 | Qiao |
| 2012/0229615 A1 | 9/2012 | Kirma |
| 2012/0232340 A1 | 9/2012 | Levy |
| 2012/0232342 A1 | 9/2012 | Reydel |
| 2012/0232343 A1 | 9/2012 | Levy |
| 2012/0253121 A1 | 10/2012 | Kitano |
| 2012/0253284 A1 | 10/2012 | Nitsan |
| 2012/0259175 A1 | 10/2012 | Reydel |
| 2012/0265094 A1 | 10/2012 | Goldfarb |
| 2013/0012778 A1 | 1/2013 | Bayer |
| 2013/0012794 A1 | 1/2013 | Zeng |
| 2013/0060086 A1 | 3/2013 | Talbert |
| 2013/0109916 A1 | 5/2013 | Levy |
| 2013/0109918 A1 | 5/2013 | Pagan |
| 2013/0110003 A1 | 5/2013 | Surti |
| 2013/0131445 A1 | 5/2013 | Zerfas |
| 2013/0131447 A1 | 5/2013 | Benning |
| 2013/0131454 A1 | 5/2013 | McCormack |
| 2013/0137930 A1 | 5/2013 | Menabde |
| 2013/0172670 A1 | 7/2013 | Levy |
| 2013/0172673 A1 | 7/2013 | Kennedy |
| 2013/0172674 A1 | 7/2013 | Kennedy |
| 2013/0172677 A1 | 7/2013 | Kennedy |
| 2013/0172678 A1 | 7/2013 | Kennedy |
| 2013/0190561 A1 | 7/2013 | Oskin |
| 2013/0194404 A1 | 8/2013 | Christiansen |
| 2013/0204088 A1 | 8/2013 | Miyamoto |
| 2013/0253272 A1 | 9/2013 | Takahashi |
| 2013/0314521 A1 | 11/2013 | Satake |
| 2013/0317295 A1 | 11/2013 | Morse |

FOREIGN PATENT DOCUMENTS

| | | |
|---|---|---|
| CN | 101061940 | 6/2011 |
| DE | 102005008153 A1 | 11/2005 |
| EP | 0029555 A2 | 6/1981 |
| EP | 543738 A1 | 5/1993 |
| EP | 730844 | 9/1996 |
| EP | 1195630 A2 | 4/2002 |
| EP | 1325458 | 7/2003 |
| EP | 1347702 A2 | 10/2003 |
| EP | 948283 B1 | 4/2004 |
| EP | 1535565 | 6/2005 |
| EP | 1073365 B1 | 7/2005 |
| EP | 1627595 A1 | 2/2006 |
| EP | 668738 B1 | 6/2006 |
| EP | 1472972 B1 | 10/2006 |
| EP | 1790280 A1 | 5/2007 |
| EP | 1834572 A1 | 9/2007 |
| EP | 1952750 | 8/2008 |
| EP | 1977675 | 10/2008 |
| EP | 1977682 A2 | 10/2008 |
| EP | 1974000653 | 10/2008 |
| EP | 1992292 A1 | 11/2008 |
| EP | 2022389 A1 | 2/2009 |
| EP | 2144571 A2 | 1/2010 |
| EP | 2276389 A1 | 1/2011 |
| EP | 1835847 B1 | 5/2011 |
| EP | 1870014 B1 | 1/2012 |

(56) References Cited

FOREIGN PATENT DOCUMENTS

| | | |
|---|---|---|
| EP | 2501271 A1 | 9/2012 |
| EP | 2503933 A1 | 10/2012 |
| EP | 2512577 A2 | 10/2012 |
| EP | 2529660 A1 | 12/2012 |
| EP | 2596756 A1 | 5/2013 |
| EP | 2623019 A1 | 8/2013 |
| GB | 2352922 A | 2/2001 |
| JP | 55078932 | 6/1980 |
| JP | 61055657 | 11/1986 |
| JP | 5049000594 | 3/1993 |
| JP | 6105000800 | 4/1994 |
| JP | 7000000352 | 1/1995 |
| JP | 8122000657 | 5/1996 |
| JP | 1013007179 | 4/1998 |
| JP | 1015001113 | 6/1998 |
| JP | 11137512 | 5/1999 |
| JP | 1116009340 | 6/1999 |
| JP | 1116009341 | 6/1999 |
| JP | 2000171727 A | 6/2000 |
| JP | 2001061762 | 3/2001 |
| JP | 2001198086 | 7/2001 |
| JP | 2002000559 | 1/2002 |
| JP | 2002058636 | 2/2002 |
| JP | 2002065575 | 3/2002 |
| JP | 2002078675 | 3/2002 |
| JP | 2002216902 | 8/2002 |
| JP | 2003038431 | 2/2003 |
| JP | 2003061900 | 3/2003 |
| JP | 2003111724 | 4/2003 |
| JP | 2003190082 | 7/2003 |
| JP | 2003220017 | 8/2003 |
| JP | 2003245247 | 9/2003 |
| JP | 2004022391 | 1/2004 |
| JP | 2004049754 | 2/2004 |
| JP | 2004049756 | 2/2004 |
| JP | 2004129834 | 4/2004 |
| JP | 2005013557 A | 1/2005 |
| JP | 2005058547 | 3/2005 |
| JP | 2005253543 | 9/2005 |
| JP | 2006068109 A | 3/2006 |
| JP | 2006218155 | 8/2006 |
| JP | 2007020866 A | 2/2007 |
| JP | 2007185276 | 7/2007 |
| JP | 2008161569 A | 7/2008 |
| JP | 2008229204 | 10/2008 |
| JP | 2009233186 | 10/2009 |
| JP | 2010178766 A | 8/2010 |
| WO | 9219148 A1 | 11/1992 |
| WO | 0052643 A1 | 9/2000 |
| WO | 0245595 | 6/2002 |
| WO | 2004026125 | 4/2004 |
| WO | 2005082228 A1 | 9/2005 |
| WO | 2006073581 | 7/2006 |
| WO | 2006105932 A1 | 10/2006 |
| WO | 2007113801 A2 | 10/2007 |
| WO | 2007136859 A2 | 11/2007 |
| WO | 2008012813 A1 | 1/2008 |
| WO | 2008073243 | 6/2008 |
| WO | 2008093288 | 8/2008 |
| WO | 2008139770 | 11/2008 |
| WO | 2008155776 | 12/2008 |
| WO | 2008156623 | 12/2008 |
| WO | 2009009414 | 1/2009 |
| WO | 2009025843 | 2/2009 |
| WO | 2009040744 | 4/2009 |
| WO | 2009095915 | 8/2009 |
| WO | 2010028612 | 3/2010 |
| WO | 2010045406 | 4/2010 |
| WO | 2010066788 | 6/2010 |
| WO | 2010146587 | 12/2010 |
| WO | 2010146587 A1 | 12/2010 |
| WO | 2011008922 | 1/2011 |
| WO | 2011083451 | 7/2011 |
| WO | 2011126812 | 10/2011 |
| WO | 2012038958 | 3/2012 |
| WO | 2012056453 | 5/2012 |
| WO | 2012077116 | 6/2012 |
| WO | 2012077117 | 6/2012 |
| WO | 2012088201 A2 | 6/2012 |
| WO | 2012103266 | 8/2012 |
| WO | 2012120507 | 9/2012 |
| WO | 2012153324 | 11/2012 |
| WO | 2013014673 | 1/2013 |
| WO | 2013024476 | 2/2013 |
| WO | 2013043704 | 3/2013 |
| WO | 2013128136 | 9/2013 |
| WO | 2013131578 | 9/2013 |
| WO | 2013144944 | 10/2013 |
| WO | 2014061023 | 4/2014 |

OTHER PUBLICATIONS

Brochure for US Endoscopy's AquaShield Water Bottle System, 2010.
First Image of an Endo Smart Cap, made by Medivators, and obtained from http://www.bymemedical.com/prod/145L.jpg and advertised at http://www.medivators.com/products/endoscopy-procedure-products/irrigation-tubing/endo-smartcap%C2%AE.
Office Action dated Feb. 27, 2014 for U.S. Appl. No. 13/557,114.
Second Image of an Endo Smart Cap, made by Medivators, and obtained from http://www.bymemedical.com/prod/150L.jpg and advertised at http://www.medivators.com/products/endoscopy-procedure-products/irrigation-tubing/endo-smartcap%C2%AE.
International Search Report of PCT/IL2011/000745, dated May 8, 2012.
International Search Report for PCT/IL2011/000832, May 16, 2012.
International Search Report for PCT/IL2011/050049, May 15, 2012.
International Search Report for PCT/IL2011/050050, May 16, 2012.
International Search Report for PCT/IL2012/050037, Jun. 1, 2012.
International Search Report for PCT/IL2012/050274, Nov. 15, 2012.
International Search Report for PCT/IL2012/050299, Nov. 15, 2012.
International Search Report for PCT/IL2013/050840, Feb. 2, 2014.
International Search Report of PCT/IL10/00476 mailed Sep. 27, 2010, 2 pages.
Office Action dated Apr. 3, 2014 for U.S. Appl. No. 13/413,141.
Office Action dated Feb. 24, 2014 for U.S. Appl. No. 13/190,968.
Office Action dated Jul. 1, 2014 for U.S. Appl. No. 13/655,120.
Office Action dated Jul. 31, 2014 for U.S. Appl. No. 13/713,449.
Office Action dated Jun. 12, 2014 for U.S. Appl. No. 13/713,466.
Office Action dated Mar. 28, 2014 for U.S. Appl. No. 13/413,252.
Office Action dated May 27, 2014 for U.S. Appl. No. 13/212,627.
Office Action dated May 30, 2014 for U.S. Appl. No. 13/119,032.
Office Action dated May 9, 2014 for U.S. Appl. No. 13/413,059.
Notice of Allowance dated Jun. 8, 2015 for U.S. Appl. No. 13/984,028.
Notice of Allowance dated Jun. 8, 2015 for U.S. Appl. No. 13/413,252.
Prosecution File History for U.S. Appl. No. 13/190,968, Jul. 26, 2011 through Jun. 17, 2015.
Notice of Allowance dated Jun. 17, 2015 for U.S. Appl. No. 13/190,968.

* cited by examiner

FLUID CHANNELING COMPONENT OF A MULTI-CAMERA ENDOSCOPE

CROSS REFERENCE

The present application is a national stage application of PCT/IL2011/050050, which was filed on Dec. 8, 2011, and relies on U.S. Patent Provisional No. 61/421,240, filed on Dec. 9, 2010 for priority. All of the aforementioned applications are herein incorporated by reference.

FIELD

Embodiments of the disclosure relate to a multi-camera endoscope having a flexible electronic circuit board.

BACKGROUND

Endoscopes have attained great acceptance within the medical community, since they provide a means for performing procedures with minimal patient trauma, while enabling the physician to view the internal anatomy of the patient. Over the years, numerous endoscopes have been developed and categorized according to specific applications, such as cystoscopy, colonoscopy, laparoscopy, upper GI endoscopy and others. Endoscopes may be inserted into the body's natural orifices or through an incision in the skin.

An endoscope is usually an elongated tubular shaft, rigid or flexible, having a video camera or a fiber optic lens assembly at its distal end. The shaft is connected to a handle, which sometimes includes an ocular for direct viewing. Viewing is also usually possible via an external screen. Various surgical tools may be inserted through a working channel in the endoscope for performing different surgical procedures.

Endoscopes, such as colonoscopes, that are currently being used, typically have a front camera for viewing the internal organ, such as the colon, an illuminator, a fluid injector for cleaning the camera lens and sometimes also the illuminator and a working channel for insertion of surgical tools, for example, for removing polyps found in the colon. Often, endoscopes also have fluid injectors ("jet") for cleaning a body cavity, such as the colon, into which they are inserted. The illuminators commonly used are fiber optics which transmit light, generated remotely, to the endoscope tip section. The use of light-emitting diodes (LEDs) for illumination is also known.

Among the disadvantages of such endoscopes, are their limited field of view and their complicated packing of all the required elements, such as electronics and fiber optics together with fluid carrying elements in the small sized endoscope tip section.

There is thus a need in the art for endoscopes, such as colonoscopies, that allow a broader field of view and also enable the efficient packing of all necessary elements in the tip section, while maintaining their function.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

According to some embodiments, there is provided herein a fluid channeling component for a tip section of a multi-camera endoscope, the fluid channeling component comprising: one or more fluid channels configured to flow insufflation and/or irrigation fluid; and one or more support elements adapted to receive, support and/or secure a flexible electronic circuit board and/or one or more of a front camera, a side camera, an optical assembly, and a light source attached to the flexible electronic circuit board.

The one or more support elements comprise one or more camera holders may be configured to directly or indirectly support a front and/or a side looking camera and/or an optical assembly thereof. The one or more camera holders may be configured to indirectly support the front and/or side looking camera via a camera bridge element. The one or more front portions may be configured to support one or more front light source surfaces of the flexible electronic circuit board.

The fluid channeling component may include, on each of two opposing side portions thereof, one or more openings for receiving side light sources. The fluid channeling component may further include, on each of the two opposing side portions thereof, an opening to receive a side looking camera, located between two openings for receiving the side light sources. The fluid channeling component may further include a front opening of the one or more fluid channels, for cleaning the front camera, the optical assembly thereof and/or one or more front light source. The fluid channeling component may further include one or more side openings of the one or more fluid channels, for cleaning one or more of the side cameras, the optical assembly thereof and/or one or more side light source. The fluid channeling component may further include a working channel adapted for the insertion of a medical tool.

The fluid channeling component may further include a groove configured to accommodate a jet fluid tube cleaning a body cavity into which the endoscope is inserted. The fluid channeling component may further include a jet fluid channel for transferring therethrough fluid for cleaning a body cavity into which the endoscope is inserted. The fluid channeling component may be configured to be used as a heat sink for one or more of the side and front illuminators. The fluid channeling component may be a unitary component comprising a front fluid channel leading to a front opening at a distal end of the unitary fluid channeling component, for cleaning one or more front optical elements (such as an optical assembly of a camera, for example a lens, an illuminator, such as a LED or a window covering an illuminator) of the tip section, and a side fluid channel leading to a left side opening and to a right side opening in the unitary fluid channeling component, for cleaning side optical elements of the tip section.

According to some embodiments, there is provided herein a tip section of a multi-camera endoscope, the tip section comprising a fluid channeling component for a tip section of a multi-camera endoscope, the fluid channeling component comprising one or more fluid channels configured for flowing for insufflation and/or irrigation fluid, and one or more support elements adapted to receive, support and/or secure a flexible electronic circuit board and/or one or more of a front camera, a side camera, an optical assembly, and a light source attached thereto; and a folded flexible electronic circuit board.

According to some embodiments, the flexible electronic circuit board comprises: a front camera surface configured to carry a forward looking camera, a first side camera surface configured to carry a first side looking camera, a second side camera surface configured to carry a second side looking camera, one or more front illuminator surfaces configured to carry one or more front illuminators to essentially illuminate the Field Of View (FOV) of the forward looking camera, one or more side illuminator surfaces configured to carry one or more side illuminators to essentially illuminate the FOV of the first side looking camera, and one or more side illuminator surfaces configured to carry one or more side illuminators to essentially illuminate the FOV of the second side looking camera. The one or more front illuminator surfaces may include three front illuminator surfaces. The front camera surface and the one or more front illuminator surfaces may be essentially parallel to each other, and essentially perpendicular to a center portion of the flexible electronic circuit board, when the flexible electronic circuit board is in a folded configuration. The first side camera surface and the second side camera surface may be essentially parallel to each other, such that the first side looking camera and the second side looking camera are directed to opposing sides. The first side camera surface and the second side camera surface may be essentially perpendicular to a center portion of the flexible electronic circuit board. The first side camera surface and the second side camera surface may be essentially perpendicular to the front camera surface.

The one or more side illuminator surfaces may include two side illuminator surfaces. The two side illuminator surfaces may be configured to carry two side illuminators to essentially illuminate the FOV of the first side looking camera, and wherein, when the flexible electronic circuit board is in a folded configuration, the two side illuminator surfaces are essentially parallel to each other and essentially perpendicular to the first side camera surface, which is located between them. The two side illuminator surfaces may be configured to carry two side illuminators on sides thereof which are facing the first side looking camera.

The two side illuminator surfaces are configured to carry two side illuminators to essentially illuminate the FOV of the second side looking camera, and wherein, when the flexible electronic circuit board is in a folded configuration, the two side illuminator surfaces are essentially parallel to each other and essentially perpendicular to the second side camera surface, which is located between them. The two side illuminator surfaces are configured to carry two side illuminators on sides thereof which are facing the second side looking camera.

The one or more support elements may include one or more camera holders configured to directly or indirectly support a front and/or a side looking camera and/or an optical assembly thereof. The one or more camera holders may be configured to indirectly support the front and/or side looking camera via a camera bridge element. The one or more support elements may include one or more front portions configured to support one or more front light source surfaces of the flexible electronic circuit board.

According to some embodiment, the fluid channeling component may include, on each of two opposing side portions thereof, one or more openings for receiving side light sources. The fluid channeling component may further include, on each of the two opposing side portions thereof, an opening to receive a side looking camera, located between two openings for receiving the side light sources.

The fluid channeling component may further include a front opening of the one or more fluid channels, for cleaning the front camera, the optical assembly thereof and/or one or more front light source.

The fluid channeling component may further include one or more side openings of the one or more fluid channels, for cleaning one or more of the side cameras, the optical assembly thereof and/or one or more side light source. The fluid channeling component may further include a working channel adapted for the insertion of a medical tool.

The fluid channeling component may further include a groove configured to accommodate a jet fluid tube for cleaning a body cavity into which the endoscope is inserted. The fluid channeling component may further include a jet fluid channel for transferring therethrough fluid for cleaning a body cavity into which the endoscope is inserted.

The fluid channeling component may be configured to be used as a heat sink for one or more of the side and front illuminators.

The fluid channeling component may be a unitary component comprising a front fluid channel leading to a front opening at a distal end of the unitary fluid channeling component, for cleaning one or more front optical elements of the tip section, and a side fluid channel leading to a left side opening and to a right side opening in the unitary fluid channeling component, for cleaning side optical elements of the tip section.

According to some embodiments, the tip section has having a diameter of about 17 mm or less. According to some embodiments, the tip section has having a diameter of about 12 mm or less. According to some embodiments, the tip section has having a diameter of about 10 mm or less.

According to some embodiments, there is provided herein a multi-camera endoscope, such as a colonoscope, comprising the tip section disclosed herein. According to some embodiments, the tip section of an endoscope (such as a colonoscope) is the most distal part of the endoscope which terminates the endoscope. The tip section is turnable by way of a bending section connected thereto.

More details and features of the current invention and its embodiments may be found in the description and the attached drawings.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. It is intended that the embodiments and figures disclosed herein are to be considered illustrative rather than restrictive. The figures are listed below.

DETAILED DESCRIPTION

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

In the description and claims of the application, each of the words "comprise" "include" and "have", and forms thereof, are not necessarily limited to members in a list with which the words may be associated.

Figure 1:
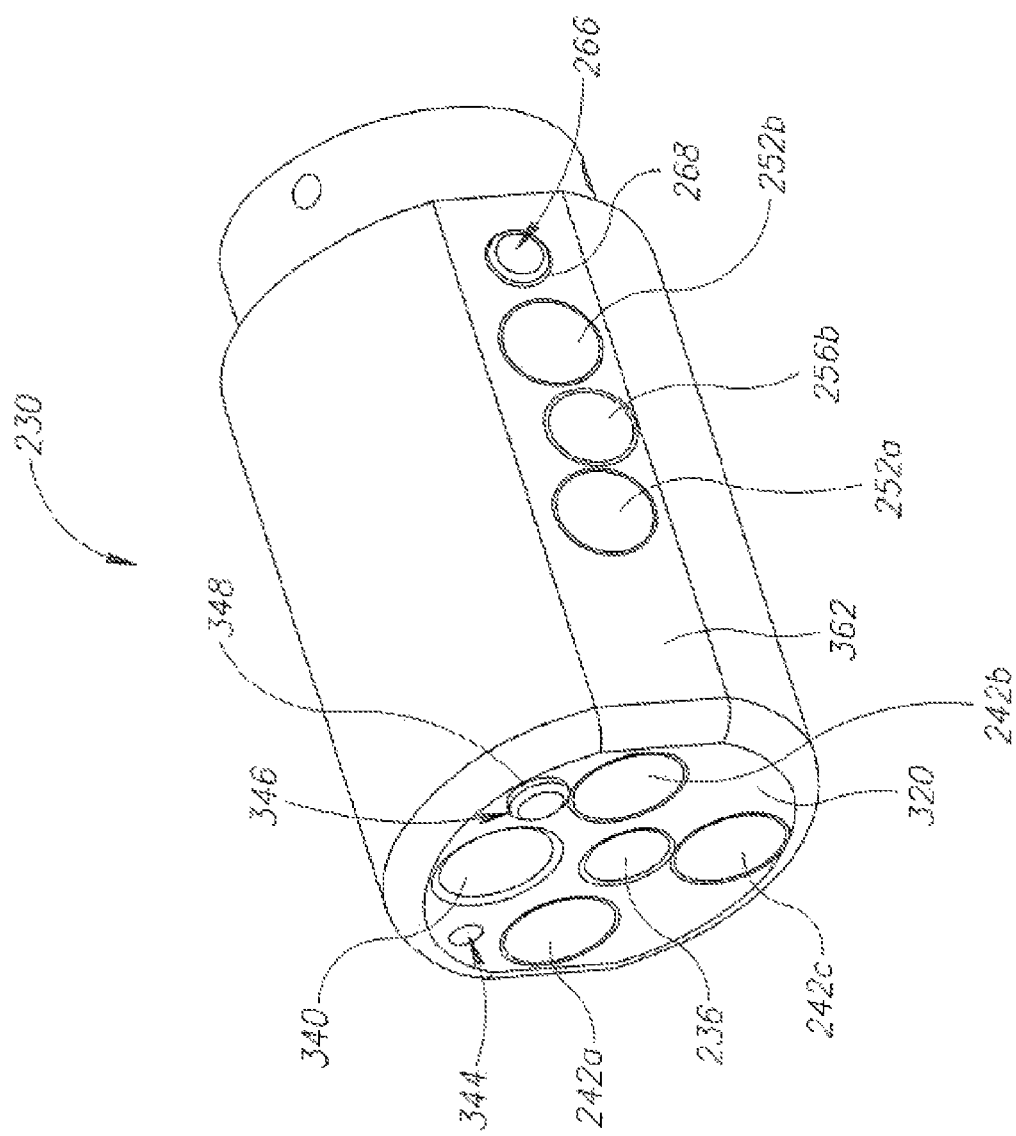
FIG. 1 schematically depicts an external isometric view of a tip section of an endoscope having multiple fields of view, according to an exemplary embodiment of the current invention.

FIG. 1 schematically depicts an external isometric view of a tip section of an endoscope having multiple fields of view according to an exemplary embodiment of the current invention.

According to an exemplary embodiment of the current invention, tip section 230 of an endoscope which comprises at least a forwards looking camera and at least one side looking camera. Tip section 230 is turnable by way of flexible shaft (not shown) which may also be referred to as a bending section, for example a vertebra mechanism).

In some embodiments, the front-looking camera and/or any of the side-looking cameras comprises a Charge Coupled Device (CCD) or a Complementary Metal Oxide Semiconductor (CMOS) image sensor.

It is noted that the term "endoscope" as mentioned to herein may refer particularly to a colonoscope, according to some embodiments, but is not limited only to colonoscopes. The term "endoscope" may refer to any instrument used to examine the interior of a hollow organ or cavity of the body.

Tip section 230 includes front optical assembly 236 of forwards looking camera 116 (seen for example in FIGS. 2 and 5-8) on the front face 320 of tip section 230. Optical axis of forwards looking camera 116 is substantially directed along the long dimension of the endoscope. However, since forward looking camera 116 is typically a wide angle camera, its Field Of View (FOV) may include viewing directions at large angles to its optical axis. Additionally, optical windows 242a, 242b and 242c of LEDs 240a, 240b and 240c, respectively, (seen for example in FIGS. 2 and 5-8) are also located on front face 320 of tip section 230. It should be noted that number of illumination sources such as LEDs used for illumination of the FOV may vary (for example, 1-5 LEDs may be used on front face 320 of tip section 230). Distal opening 340 of a working channel (not shown) is also located on front face 320 of tip section 230, such that a surgical tool inserted through working channel tube, and through the working channel in the endoscope's tip section 230 and deployed beyond front face 320 may be viewed by forwards looking camera 116.

Distal opening 344 of a jet fluid channel is also located on front face 320 of tip section 230. Distal opening 344 of a jet fluid channel may be used for providing high pressure jet of fluid such as water or saline for cleaning the walls of the body cavity.

Also located on front face 320 of tip section 230 is an irrigation and insufflation (I/I) injector 346 having a nozzle 348 aimed at front optical assembly 236. I/I injector 346 may be used for injecting fluid (liquid and/or gas) to wash contaminants such as blood, feces and other debris from front optical assembly 236 of forwards looking camera. Optionally the same injector is used for cleaning front optical assembly 236 and one two or all of optical windows 242a, 242b and 242c. I/I injector 346 may be fed by fluid such as water and/or gas which may be used for cleaning and/or inflating a body cavity.

Visible on the side wall 362 of tip section 230 is the side camera (side looking camera) element 256b of side looking camera 220b and optical windows 252a and 252b of LEDs 250a and 250b for camera 220b. A second side looking camera, 220a, is not shown in FIG. 1 but can be seen for example in FIGS. 2 and 5-6, along with its optical assemblies 256a and optical windows 252a' and 252b' of LEDs 250a' and 250b' of camera 220a. Optical axis of side looking camera 220a is substantially directed perpendicular to the long dimension of the endoscope. Optical axis of side looking camera 220b is substantially directed perpendicular to the long dimension of the endoscope. However, since side looking cameras 220a and 220b is typically a wide angle camera, its field of view may include viewing directions at large angles to its optical axis.

I/I injector 266 having a nozzle 268 aimed at side optical assembly 256b may be used for injecting fluid to wash contaminants such as blood, feces and other debris from side optical assembly 256b of side looking camera. The fluid may include gas which may be used for inflating a body cavity. Optionally the same injector is used for cleaning both side optical assembly 256b and optical windows 252a and/or 252b. It is noted that according to some embodiments, the tip may include more than one window and LEDs, on the side and more than one window and LEDs in the front (for example, 1-5 windows and two LEDs on the side). Similar configuration of I/I injector and nozzle exists for cleaning optical assembly 256a and optical windows 252a' and 252b' located on the other side of tip 230. The I/I injectors are configured to clean all or a part of these windows/LEDs. I/I injectors 346 and 266 may be fed from same channel.

It is noted that the side wall 362 has a form of an essentially flat surface which assists in directing the cleaning fluid injected from I/I injector 266 towards side optical assembly 256b and optical windows 252a and/or 252b. Lack of such flat surface may result in dripping of the cleaning fluid along the curved surface of tip section 230 of the endoscope without performing the desired cleaning action.

It should be noted that while only one side looking camera is seen in FIG. 1, preferably at least two side looking cameras may be located within tip section 230. When two side looking cameras are used, the side looking cameras are preferably installed such that their field of views are substantially opposing. However, different configurations and number of side looking cameras are possible within the general scope of the current invention.

A significant problem always existed in the art when attempts were made to pack all necessary components into the small inner volume of the endoscope. This problem dramatically increases when three cameras and respective illumination sources (such as LEDs) should be packed in the tip of the endoscope, as disclosed herein in accordance to some embodiments of the present invention. There is thus provided, according to some embodiments of the invention, a flexible electronic circuit for carrying and packing within the limited inner volume of the endoscope's tip, at least a front camera and one or more (for example two) side view cameras and their respective illumination sources.

According to some embodiments, the flexible circuit board consumes less space and leaves more volume for additional necessary features. The flexibility of the board adds another dimension in space that can be used for components positioning.

The use of the circuit board according to embodiments of the invention can significantly increase reliability of the electric modules connection thereto as no wires are for components connectivity. In addition, according to some embodiments, the components assembly can be machined and automatic.

The use of the circuit board according to embodiments of the invention, may also allow components (parts) movement and maneuverability during assembly of the camera head (tip of the endoscope) while maintaining high level of reliability. The use of the circuit board according to embodiments of the invention, may also simplify the (tip) assembling process.

According to some embodiments, the flexible circuit board is connected to the control unit via multi wire cable; this cable is welded on the board in a designated location freeing additional space within the tip assembly and adding flexibility to cable access. Assembling the multi wire cable directly to the electrical components was a major challenge which is mitigated by the use of the flexible board according to embodiments of the invention.

Figure 2:
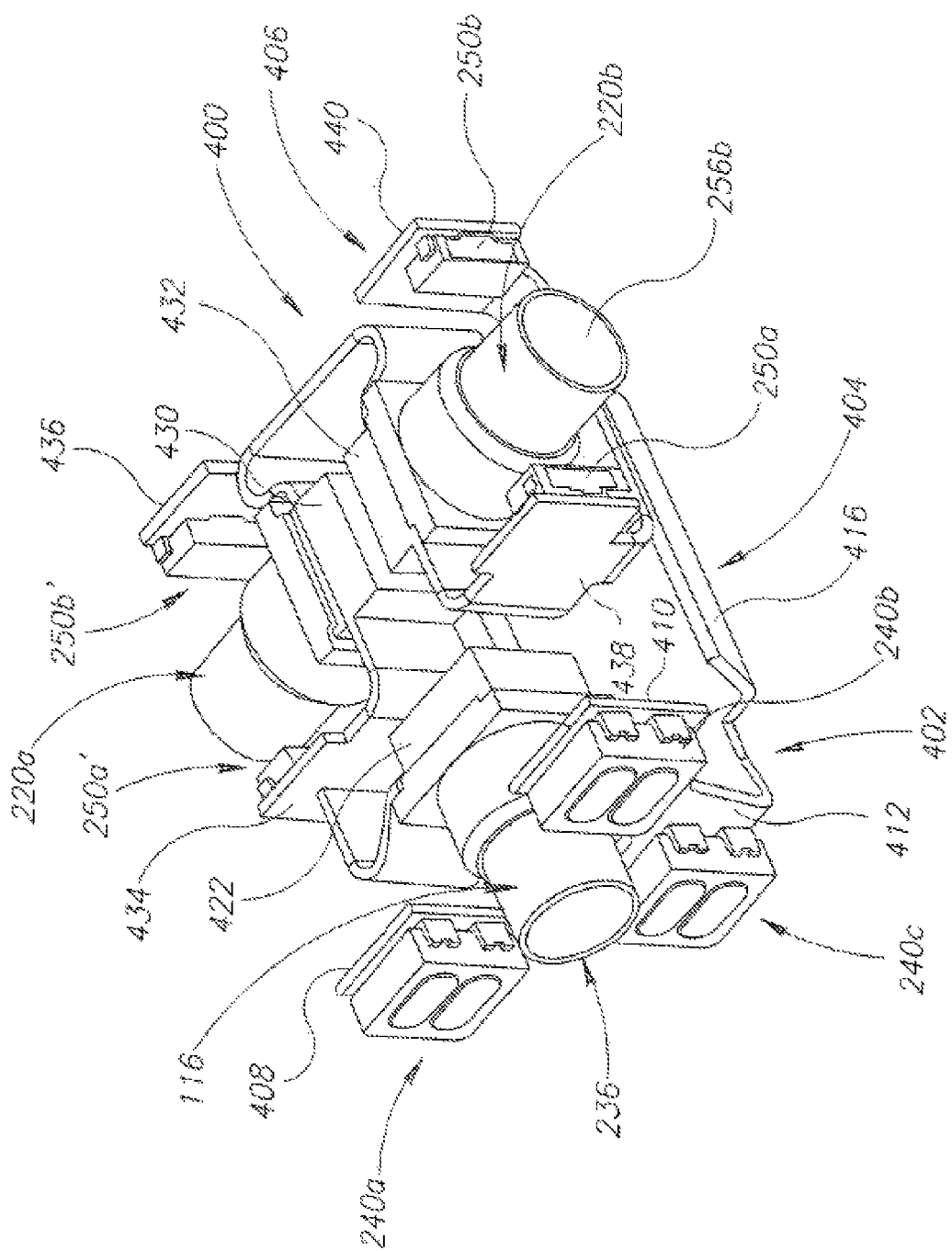
FIG. 2 schematically depicts an isometric view of a folded flexible electronic circuit board carrying a front view camera, two side view cameras and illumination sources, according to an exemplary embodiment of the current invention.

FIG. 2 schematically depicts an isometric view of a folded flexible electronic circuit board carrying a front view camera, two side view cameras and illumination sources, according to embodiments of the invention.

Flexible electronic circuit board 400, shown here in a folded configuration, is configured to carry forward looking camera 116; LEDs 240a, 240b and 240c positioned to essentially illuminate the Field Of View (FOV) of forward looking camera 116; side looking cameras 220b; LEDs 250a and 250b positioned to essentially illuminate the Field Of View (FOV) of side looking cameras 220b; side looking cameras 220a and LEDs 250a' and 250b' positioned to essentially illuminate the Field Of View (FOV) of side looking cameras 220a.

Figure 3:
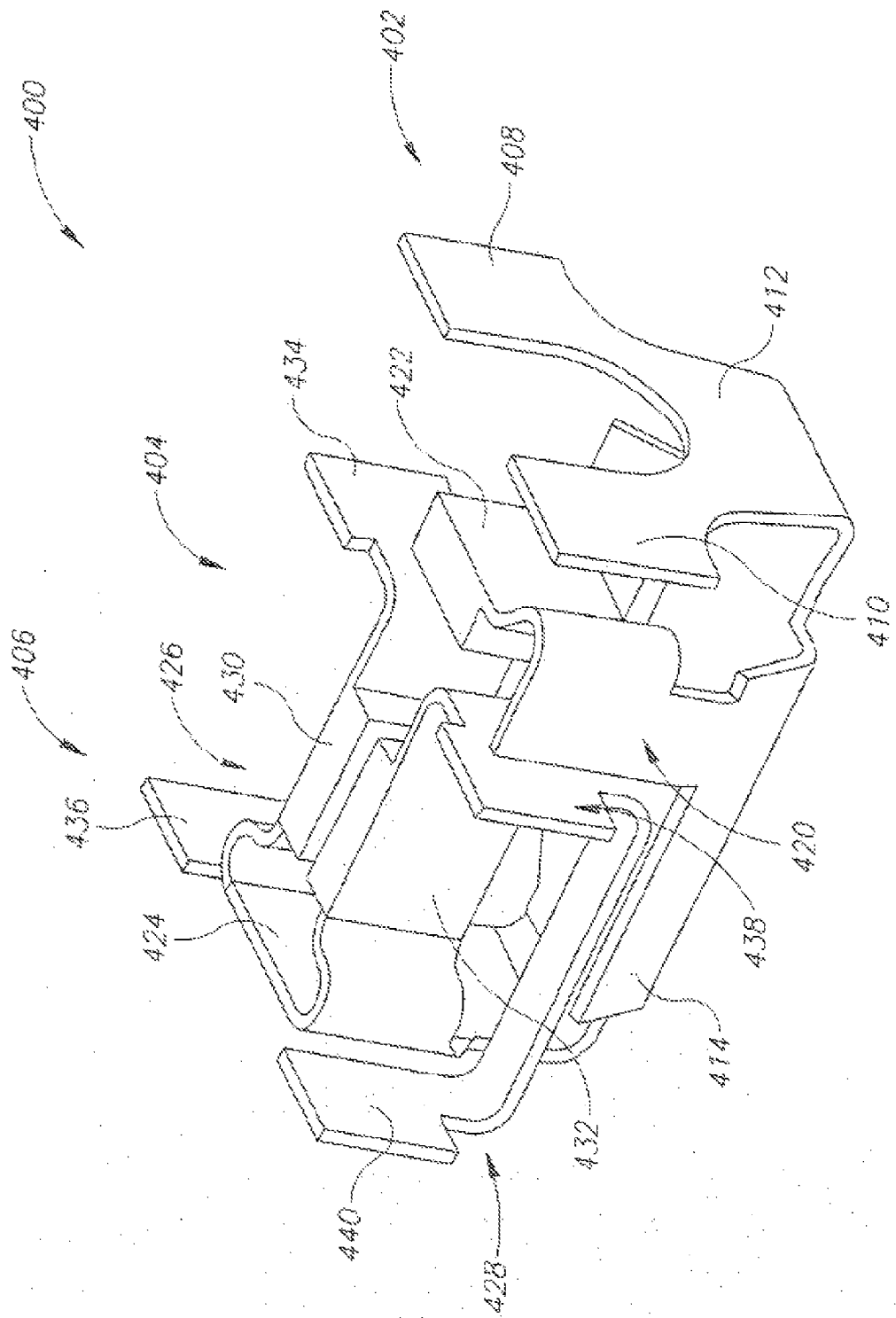
FIG. 3 schematically depicts an isometric view of a folded flexible electronic circuit board, according to an exemplary embodiment of the current invention.
Figure 4:
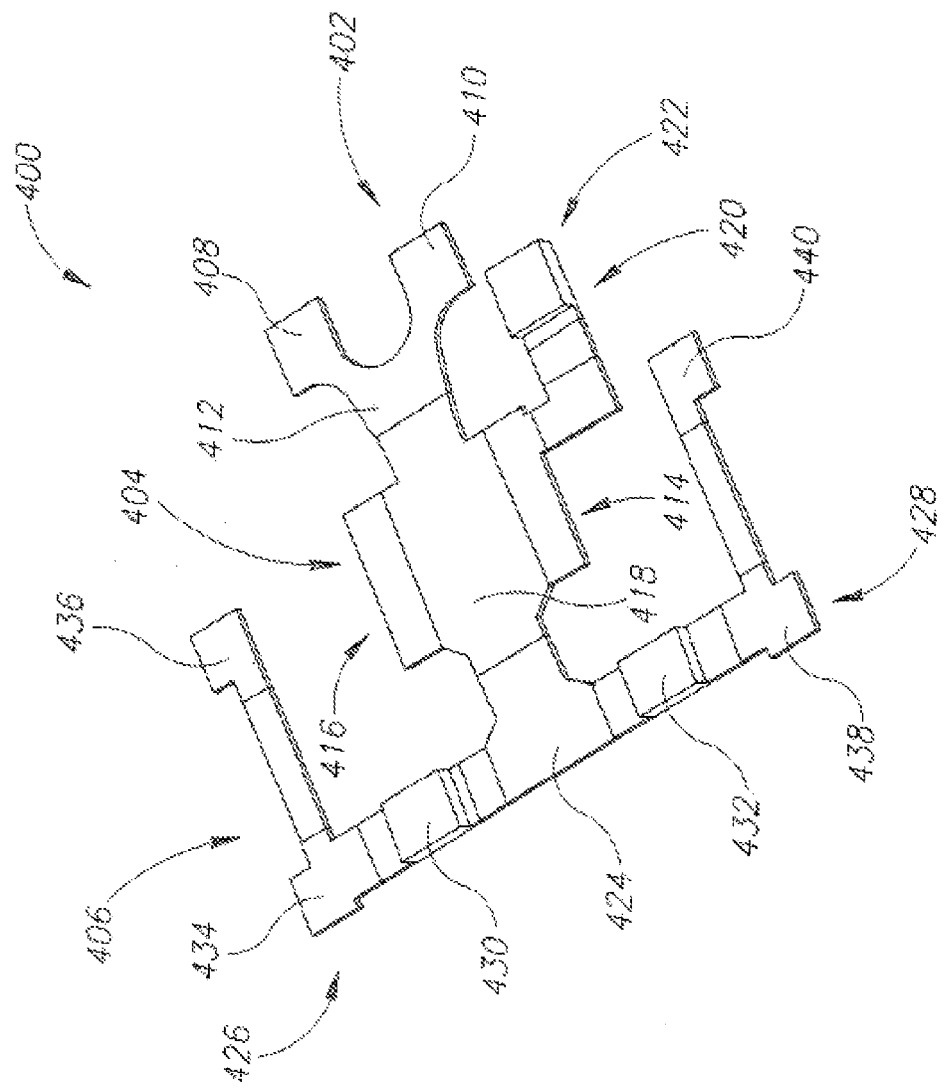
FIG. 4 schematically depicts an isometric view of a flexible electronic circuit board in an unfolded (flat) configuration, according to an exemplary embodiment of the current invention.

As can also be seen in FIGS. 3 and 4, which schematically depict isometric views of flat and folded flexible electronic circuit board, respectively, according to embodiments of the invention, flexible electronic circuit board 400 includes three sections: front section 402, main section 404 and rear section 406.

Front section 402 of flexible electronic circuit board 400 includes first front LED surface 408, second front LED surface 410 and a bottom front LED surface 412. First front LED surface 408, second front LED surface 410 and a bottom front LED surface 412 are flat surfaces formed from a unitary piece of a PCB layer. First front LED surface 408 is adapted to carry front LED 240a, second front LED surface 410 is adapted to carry front LED 240b and a bottom front LED surface 412 is adapted to carry front LED 240c. First front LED surface 408, second front LED surface 410 and a bottom front LED surface 412 form an arc shape between them which is configured to support forward looking camera 116.

Front section 402 of flexible electronic circuit board 400 is connected to main section 404 through bottom section 412. Main section 404 of flexible electronic circuit board 400 includes a center potion 418, a first foldable side panel 414 and a second foldable side panel 416. When flexible electronic circuit board 400 is in a folded configuration, first foldable side panel 414 and a second foldable side panel 416 are configured to fold upwards (towards the length axis of the endoscope tip), for example, as shown herein, forming an angle of about 45 degrees with center portion 418 of main section 404. First foldable side panel 414 also includes an arm section 420, extending therefrom, having a front sensor surface 422 (may also be referred to as a camera surface) adapted to carry forward looking camera 116. When flexible electronic circuit board 400 is in folded position, arm section 420 is folded to be essentially perpendicular to center portion 418 of main section 404, and front sensor surface 422 is folded to be essentially perpendicular to center portion 418 and to arm section 420, such that it faces forwards, essentially at the same direction of first front LED surface 408, second front LED surface 410 and a bottom front LED surface 412. This configuration enables forward looking camera 116 and LEDs 240a-c to face the same direction.

As described hereinabove, main section 404 is connected to bottom section 412 of front section 402. On the opposing end of main section 404, it is connected to rear section 406.

Rear section 406 includes a rear central portion 424. Rear central portion 424 is connected to a first rear arm section 426, extending from one side of rear central portion 424 and to a second rear arm section 428, extending from the opposing side of rear central portion 424.

First rear arm section 426 includes a first side sensor surface 430 (adapted to carry side looking camera 220a). Second rear arm section 428 includes a second side sensor surface 432 (adapted to carry side looking camera 220b).

First rear arm section 426 further includes a first side LED surface 434 and a second side LED surface 436, adapted to carry side LEDs 250a' and 250b', respectively. Second rear arm section 428 further includes a third side LED surface 438 and a fourth side LED surface 440, adapted to carry side LEDs 250a and 250b, respectively.

According to some embodiments, front sensor surface 422 (which is adapted carry forward looking camera 116), first side sensor surface 430 and second side sensor surface 432 (which are adapted carry side looking cameras 220a and 220b) are thicker than the front and side LED surfaces. For example, the sensor surface thickness is configured for locating the sensor (of the camera) such that the welding pins of the sensor wrap the surface and are welded on the opposite side of the sensor in specific welding pads.

The sensor surfaces may be rigid and used as basis for the camera assembly. The height of the sensor surface has significant importance allowing the sensor conductors to bend in a way they will directly reach the welding pads on the opposite side of the sensor rigid surface. The rigid basis also serves as electrical ground filtering electromagnetic noise to and from the sensor and thus increasing signal integrity.

When flexible electronic circuit board 400 is in a folded configuration, rear central portion 424 is folded upwards, perpendicularly to center potion 418 of main section 404. First side sensor surface 430 and second side sensor surface 432 are positioned perpendicularly to center potion 418 and also perpendicularly rear central portion 424. In addition, first side sensor surface 430 and second side sensor surface 432 are positioned essentially parallel and "back to back" to each other such that when they carry side looking camera 220a and side looking camera 220b, these cameras view opposing sides. First side LED surface 434 and a second side LED surface 436 are positioned perpendicularly to first side sensor surface 430 and adapted to carry, on their inner sides, side LEDs 250a' and 250b', respectively, such that LEDs 250a' and 250b' are positioned in proximity to side looking camera 220a. Third side LED surface 438 and a fourth side LED surface 440 are positioned perpendicularly to second side sensor surface 432 and adapted to carry, on their inner sides, side LEDs 250a and 250b, respectively, such that LEDs 250a and 250b are positioned in proximity to side looking camera 220b.

According to some embodiments of the invention, front section 402, main section 404 and rear section 406 of flexible electronic circuit board 400 are all integrally formed from a unitary piece of circuit board layer.

Figure 5:
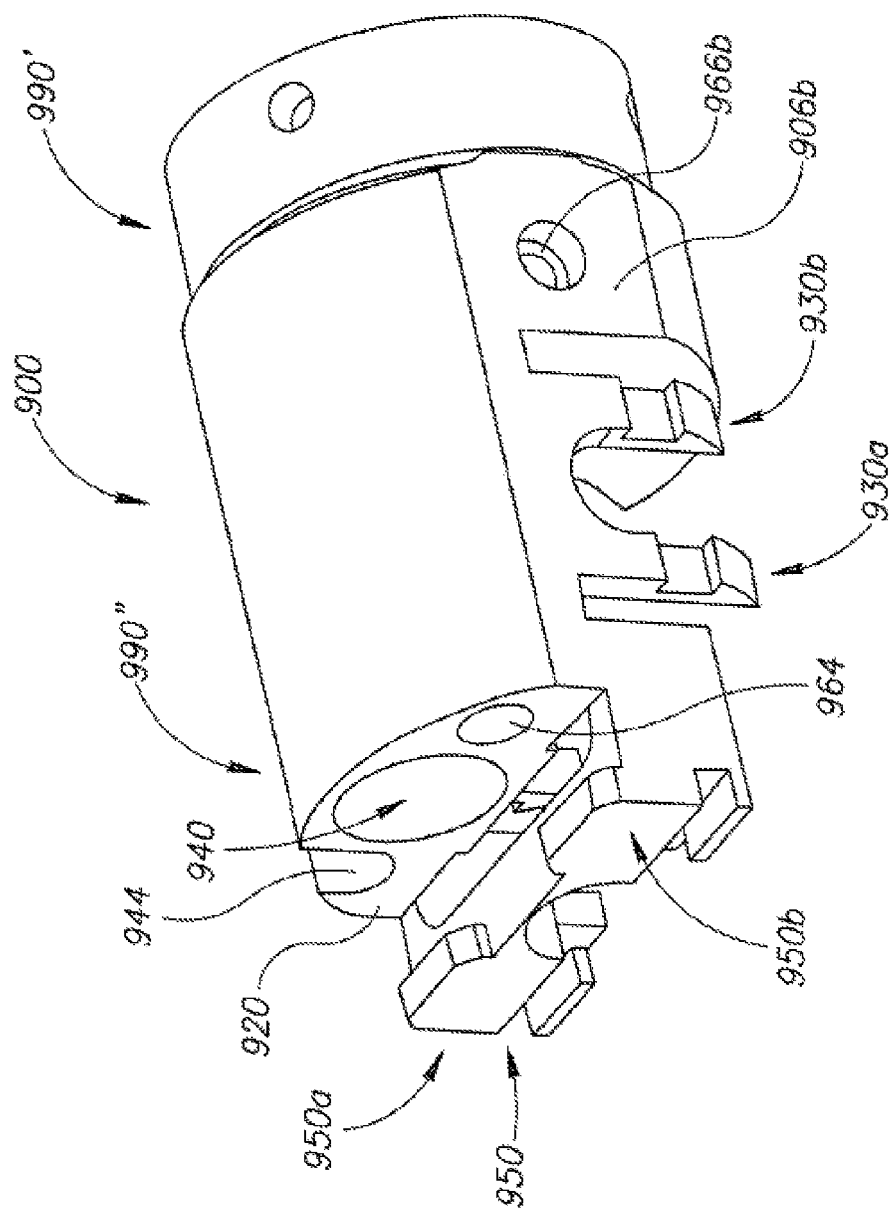
FIG. 5 schematically depicts an isometric view of a fluid channeling component combined with a flexible electronic circuit board holder, according to an exemplary embodiment of the current invention.
Figure 6:
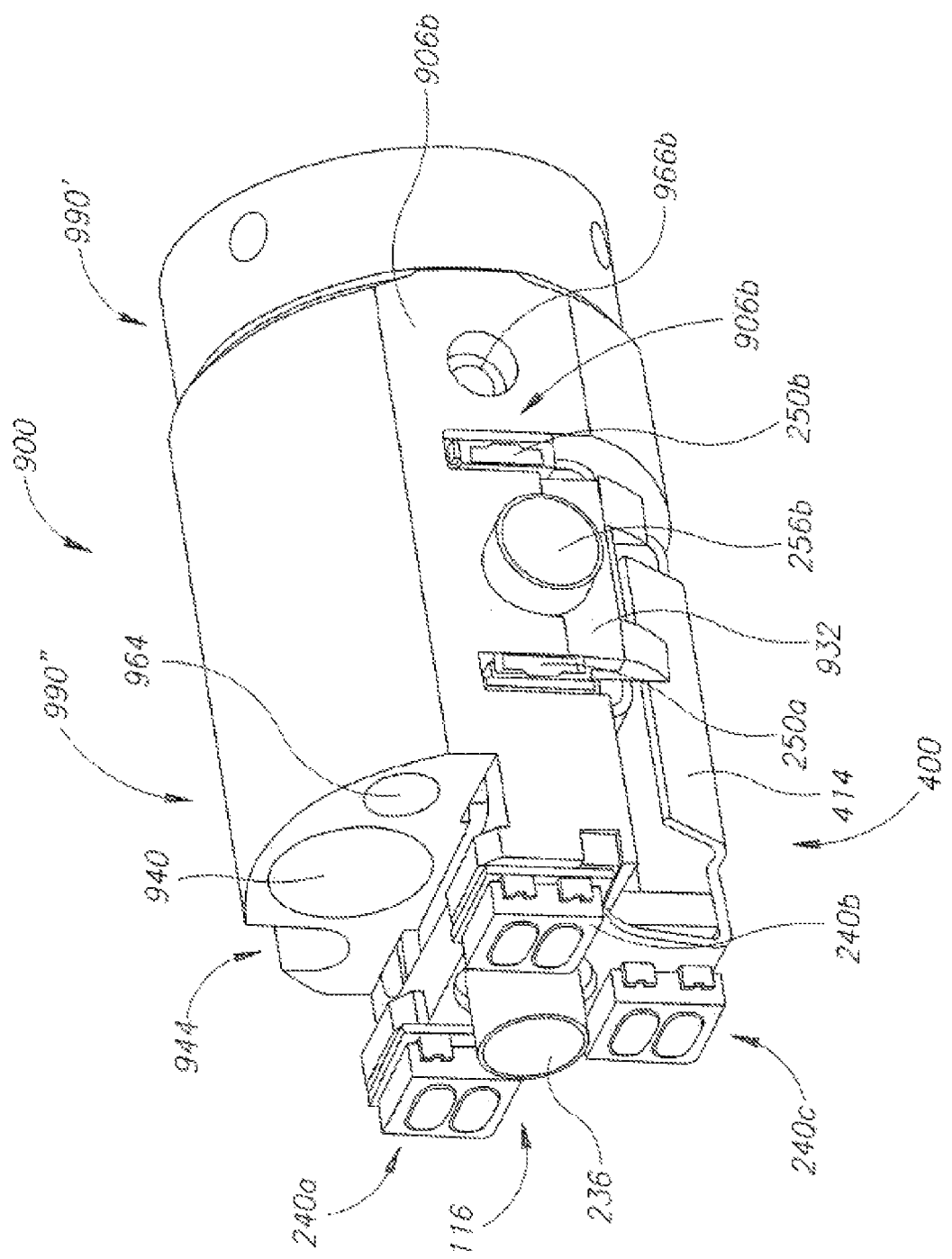
FIG. 6 schematically depicts an isometric view of a fluid channeling component combined with a flexible electronic circuit board holder and a folded flexible electronic circuit board carrying cameras and illumination sources, according to an exemplary embodiment of the current invention; and, FIG. 7 schematically depicts an isometric view of a fluid channeling component combined with a flexible electronic circuit board holder, a folded flexible electronic circuit board carrying cameras and illumination sources, and a tip cover (in an exploded view), according to an exemplary embodiment of the current invention.

Reference is now made to FIG. 5, which schematically depicts an isometric view of a fluid channeling component combined with a flexible electronic circuit board holder, according to an exemplary embodiment of the current invention and to FIG. 6, which schematically depicts an isometric view of a fluid channeling component combined with a flexible electronic circuit board holder and a folded flexible electronic circuit board carrying cameras and illumination sources, according to an exemplary embodiment of the current invention.

FIG. 5 shows a fluid channeling component 900 which also include parts enabling this component to function as a flexible electronic circuit board holder.

Fluid channeling component 900, which is also adapted to function as a flexible electronic circuit board holder is configured to separate the fluid channels and working channel, which are located in fluid channeling component 900 from the sensitive electronic and optical parts (such as cameras and LEDs) which are located in the area of flexible electronic circuit board 400 (shown in FIG. 6).

However, according to some embodiments, the fluid channeling component, (such as fluid channeling component 900), or any one of the parts thereof may be used for electric conductivity and heat transfer purposes. The fluid channeling component, according to embodiments of the invention, (such as fluid channeling component 900) can be used as a heat sink for some or all of the illuminators (such as side or front LEDs) and reduce overall temperature of the endoscope tip. This may solve or at least mitigate a major problem of raised temperatures of endoscope tip and/or any of its components, particularly when using LED illuminators. For this purpose, the fluid channeling component may be made of metal such as steel, brass, aluminum or any other material which may serve the purpose of heat transfer.

Fluid channeling component 900 (or according to some embodiments, a unitary fluid channeling component), according to some embodiments, may generally include two parts: a proximal fluid channeling component section 990' and a distal fluid channeling component section 990". Proximal fluid channeling component section 990' may have an essentially cylindrical shape. Distal channeling component section 990" may partially continue the cylindrical shape of proximal fluid channeling component section 990' and may have a shape of a partial cylinder (optionally elongated partial cylinder), having only a fraction of the cylinder (along the height axis of the cylinder), wherein another fraction of the cylinder (along the height axis of the cylinder) is missing. Distal fluid channeling component section 990" may be integrally formed as a unitary block with proximal fluid channeling component section 990'. The height of distal fluid channeling component section 990" may by higher than that of proximal fluid channeling component section 990'. In the case of distal fluid channeling component section 990", the shape of the partial cylinder (for example, partial cylinder having only a fraction of a cylinder shape along one side of the height axis) provides a space to accommodate flexible electronic circuit board 400.

Front face 920 of distal fluid channeling component section 990" includes a distal opening 940 of working channel (located inside fluid channeling component 990, not shown). Front face 920 of distal fluid channeling component section 990" further includes distal groove 944 configured to accommodate a jet fluid tube (not shown) which may be used for providing high pressure jet of fluid such as water or saline for cleaning the walls of the body cavity (such as the colon) and optionally for suction. Distal groove 944 of the jet fluid tube may be entirely embedded in fluid channeling component 900 (forming a closed channel instead of a groove, which may accommodate a jet fluid tube, or in itself flow jet fluid), or, as shown herein partially opened. Front face 920 of distal fluid channeling component section 990" further includes irrigation and insufflation (I/I) opening 964 which may be used for injecting fluid (liquid and/or gas) to wash contaminants such as blood, feces and other debris from front optical assembly 236 of forwards looking camera 116 (shown in FIG. 6).

Proximal fluid channeling component section 990' of fluid channeling component 900 includes I/I openings 966a (not shown) and 966b aimed at side optical assembly 256a and 256b, respectively, and used for injecting fluid (the term "fluid" may also include gas and/or liquid) to wash contaminants such as blood, feces and other debris from side optical assemblies 256a and 256b of side looking cameras 220a and 220b. According to some embodiments, the injectors may supply liquid for cleaning any of the tip elements (such as any optical assembly, windows, LEDs, and other elements).

As shown in FIGS. 5 and 6, fluid channeling component 900 which is also a flexible electronic circuit board holder is built as a unitary piece of rigid material, such as brass, stainless steel, aluminum or any other material. This type of fluid channeling component 900 is configured to hold flexible electronic circuit board 400 in its desired folded position, and secure the front and side looking cameras and their corresponding illuminators in place. As discussed hereinabove, and according to some embodiments, the fluid channeling component, (such as fluid channeling component 900) may be used for heat transfer purposes. The fluid channeling component, according to embodiments of the invention, (such as fluid channeling component 900) can be used as a heat sink for some or all of the illuminators (such as side or front LEDs) and/or other electronic components, and reduce overall temperature of the endoscope tip. This may solve or at least mitigate a major problem of raised temperatures of endoscope tip and/or any of its components, particularly when using LED illuminators.

Fluid channeling component 900 further includes a front portion 950 (shown here as formed as two front portions 950a and 950b), supporting the back sides (opposing to the sides where the LEDs are attached) of first front LED surface 408 and second front LED surface 410, respectively. Front portions 950a and 950b form an arc shape between them which is configured to accommodate and support forward looking camera 116. According to some embodiments front portion 950 distally protrudes from front face 920.

Fluid channeling component 900 further includes two side portions 906a (not shown) and 906b on the two opposing sides thereof. Each of side portions 906a and 906b include two small openings for the side LEDs (250a, 250b, 250a', 250b') and one opening for side looking camera 220b and 220a (not shown). Side portions 906a and 906b of fluid channeling component 900 abut first and second side foldable panels 416 and 414, respectively, of flexible electronic circuit board 400.

Each one of side portions 906a (not shown) and 906b further includes I/I openings 966a (not shown) and 966b aimed at side optical assembly 256a and 256b, respectively, and used for injecting fluid (the term "fluid" may also include gas and/or liquid) to wash contaminants such as blood, feces and other debris from side optical assemblies 256a and 256b of side looking cameras 220a and 220b. According to some embodiments, the openings may supply liquid for cleaning any of the tip elements (such as any optical assembly, windows, LEDs, and other elements).

Each one of side portions 906a (not shown) and 906b further includes two camera holders, for example camera holders 930a and 930b adapted to receive a camera bridge 932 (shown in FIG. 6) which is adapted to support assemblies 256a and 256b of side looking cameras 220a and 220b.

Similar to FIG. 2, flexible electronic circuit board 400, shown in FIG. 6 in its folded configuration, is configured to carry forward looking camera 116; LEDs 240a, 240b and 240c positioned to illuminate essentially the Field Of View (FOV) of forward looking camera 116; side looking cameras 220b; LEDs 250a and 250b positioned to illuminate essentially the Field Of View (FOV) of side looking cameras 220b; side looking cameras 220a and LEDs 250a' and 250b' positioned to illuminate essentially the Field Of View (FOV) of side looking cameras 220a.

Figure 7:
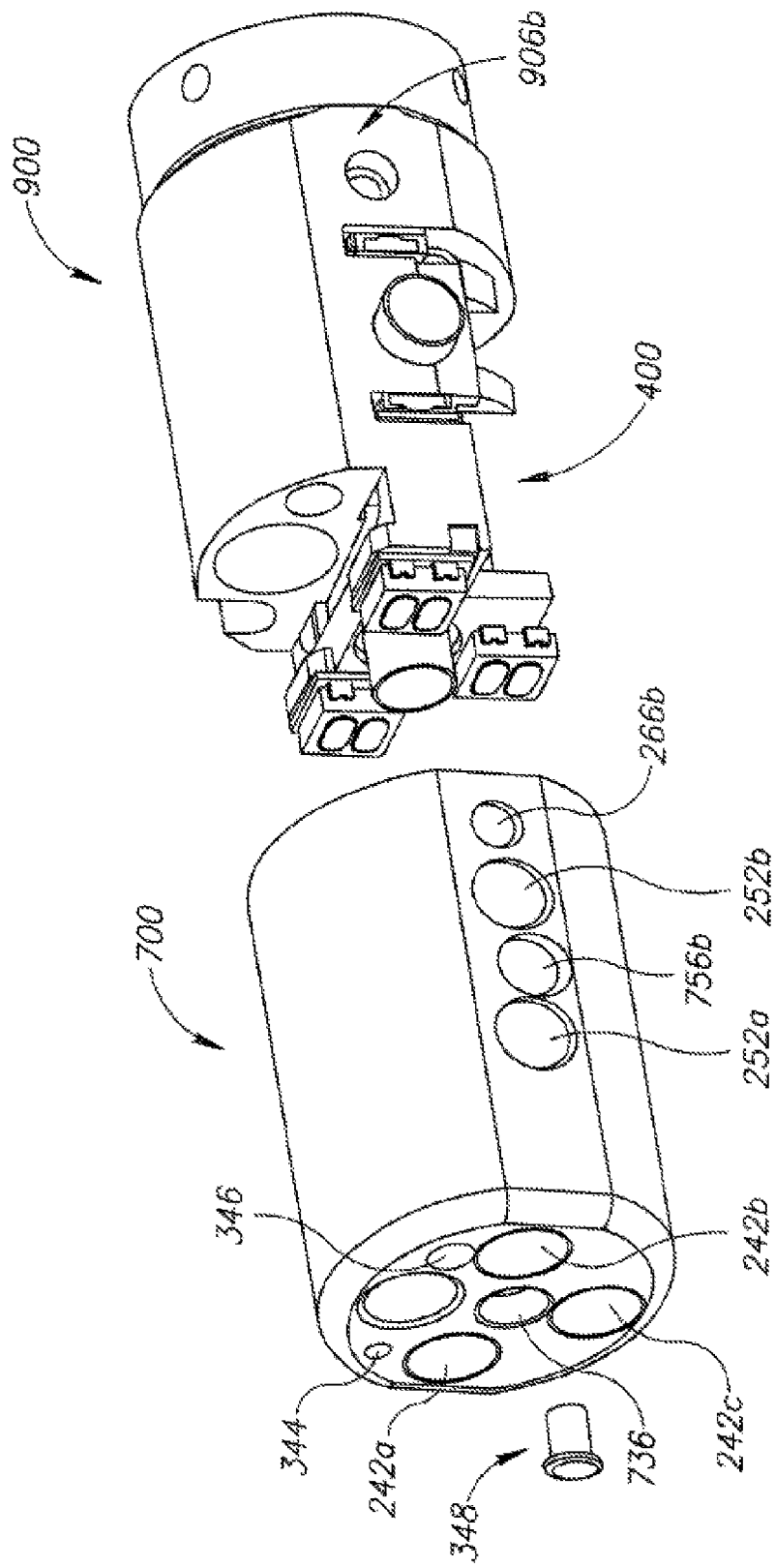

Reference is now made to FIG. 7, schematically depicts an isometric view of a fluid channeling component combined with a flexible electronic circuit board holder, a folded flexible electronic circuit board carrying cameras and illumination sources, and a tip cover (in an exploded view), according to an exemplary embodiment of the current invention.

Fluid channeling component 900 and flexible electronic circuit board 400 are described in FIGS. 5 and 6. Tip cover 700 is designed to fit over the inner parts of the tip section 230, and to provide protection to the internal components in the inner part.

Tip cover 700 includes hole 736 configured to align with front optical assembly 236 of forwards looking camera 116; optical windows 242a, 242b and 242c of LEDs 240a, 240b and 240c (seen for example in FIGS. 2 and 5-8); distal opening 340 of a working channel (not shown); distal opening 344 of a jet fluid channel; I/I injector 346 having a nozzle 348 (aligning with opening 664 of Fluid channeling component 600); holes 756a (not shown) and 756a configured to align with side optical assemblies 256a and 256b of side looking cameras 220a and 220b; optical windows 252a and 252b of LEDs 250a and 250b for camera 220a; and optical windows 252a' and 252b' of LEDs 250a' and 250b' for camera 220b; side holes 266a (not shown) and 266b adapted to align with I/I injectors 966a (not shown) and 966b.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference to the specification, to the same extent as if each individual publication, patent or patent application was specifically and individually indicated to be incorporated herein by reference. In addition, citation or identification of any reference in this application shall not be construed as an admission that such reference is available as prior art to the present invention.

What we claim is:

1. A tip section of a multi-camera endoscope, the tip section comprising:
    a front camera with a front optical assembly, a front light source, and a front sensor surface associated therewith;
    a first side camera with a first side optical assembly, and a first side sensor surface associated therewith;
    a second side camera with a second side optical assembly, and a second side sensor surface associated therewith;
    a fluid channeling component for a tip section of a multi-camera endoscope, the fluid channeling component comprising one or more fluid channels configured for flowing for insufflation and/or irrigation fluid, wherein said fluid channeling component further comprises a front opening of said one or more fluid channels for cleaning at least one of the front camera and the front light source; and
    a unitary support element, having a longitudinal central axis, adapted to support the front camera, the front optical assembly, the front sensor surface, the first side camera, the first side optical assembly, the first side sensor surface, the second side camera, second side optical assembly, and the second side sensor and comprising a planar surface and a plurality of panels extending up from, and substantially perpendicular to, the planar surface, wherein the plurality of panels are configured to attach to and position the first side sensor surface and the second side sensor surface parallel to the longitudinal central axis and attach to and position the front sensor surface perpendicular to the longitudinal central axis and wherein the unitary support element, together with the front camera, the front optical assembly, the front sensor surface, the first side camera, the first side optical assembly, the first side sensor surface, the second side camera, second side optical assembly, and the second side sensor, form a modular unit adapted to be inserted into the tip section.

2. The tip section of claim 1, wherein said fluid channeling component further comprises one or more side openings of said one or more fluid channels for cleaning said first side camera and a side light source.

3. The tip section of claim 1, wherein said fluid channeling component further comprising a working channel adapted for the insertion of a medical tool.

4. The tip section of claim 1, wherein said fluid channeling component further comprising a groove configured to accommodate a jet fluid tube for cleaning a body cavity into which said endoscope is inserted.

5. The tip section of claim 1, wherein said fluid channeling component further comprises a jet fluid channel for transferring therethrough fluid for cleaning a body cavity into which said endoscope is inserted.

6. The tip section of claim 1, wherein said fluid channeling component is configured to be used as a heat sink for at least one of the front light source and a side illuminator.

7. The tip section of claim 1, wherein said fluid channeling component is a unitary component comprising a front fluid channel leading to a front opening at a distal end of said fluid channeling component for cleaning the front camera and a side fluid channel leading to a left side opening and to a right side opening in said fluid channeling component for cleaning the first side camera and the second side camera respectively.

8. The tip section according to claim 1, wherein said fluid channeling component has a diameter of about 17 mm or less.

\* \* \* \* \*